(12) United States Patent
Chen

(10) Patent No.: US 7,105,521 B2
(45) Date of Patent: *Sep. 12, 2006

(54) EUGENOSEDIN-A BASED PHARMACOLIGICAL AGENTS

(75) Inventor: Ing-Jun Chen, Kaohsiung (TW)

(73) Assignee: Syn-Tech Chem & Pharm Co., Ltd., (TW)

( * ) Notice: Subject to any disclaimer, the term of this patent is extended or adjusted under 35 U.S.C. 154(b) by 0 days.

This patent is subject to a terminal disclaimer.

(21) Appl. No.: 10/610,900

(22) Filed: Jun. 30, 2003

(65) Prior Publication Data

US 2004/0266786 A1    Dec. 30, 2004

(51) Int. Cl.
*A61K 31/495* (2006.01)
*C07D 295/092* (2006.01)

(52) U.S. Cl. .................. 514/255.03; 544/394
(58) Field of Classification Search ............... 544/394; 514/255.03

See application file for complete search history.

(56) References Cited

U.S. PATENT DOCUMENTS 6,887,878 B1 *    5/2005    Chen ............... 514/255.03

OTHER PUBLICATIONS

Rastogi et al. J. Med. Chem. vol. 15, p. 286-291 (1972).*

* cited by examiner

*Primary Examiner*—Emily Bernhardt
(74) *Attorney, Agent, or Firm*—Derek H. Maughan; Stephen M. Nipper; Dykas, Shaver & Nipper, LLP

(57) ABSTRACT

The present invention provides isoeugenol derivative compounds having the moiety

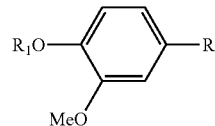

and having $\alpha_2$-adrenergic/5-$HT_{2A}$ antagonist, 5-HT re-uptake inhibition, and anti-oxidant activities.

3 Claims, 31 Drawing Sheets

1. -●- solvent control  2. -○- Eugenosedine A 0.1 mg kg$^{-1}$
3. -▼- Eugenosedine A 0.5 mg kg$^{-1}$  4. -▽- Eugenosedine A 1.0 mg kg$^{-1}$ Each point represents the mean of eight rats.
*Significantly different from control, p<0.05 [two-way repeated-measures analysis of variance (ANOVA) followed by Student-Newman-Keuls test.]

Each point represents the mean of eight rats.
*Significantly different from control, p<0.05 [two-way repeated-measures analysis of variance (ANOVA) followed by Student-Newman-Keuls test.]

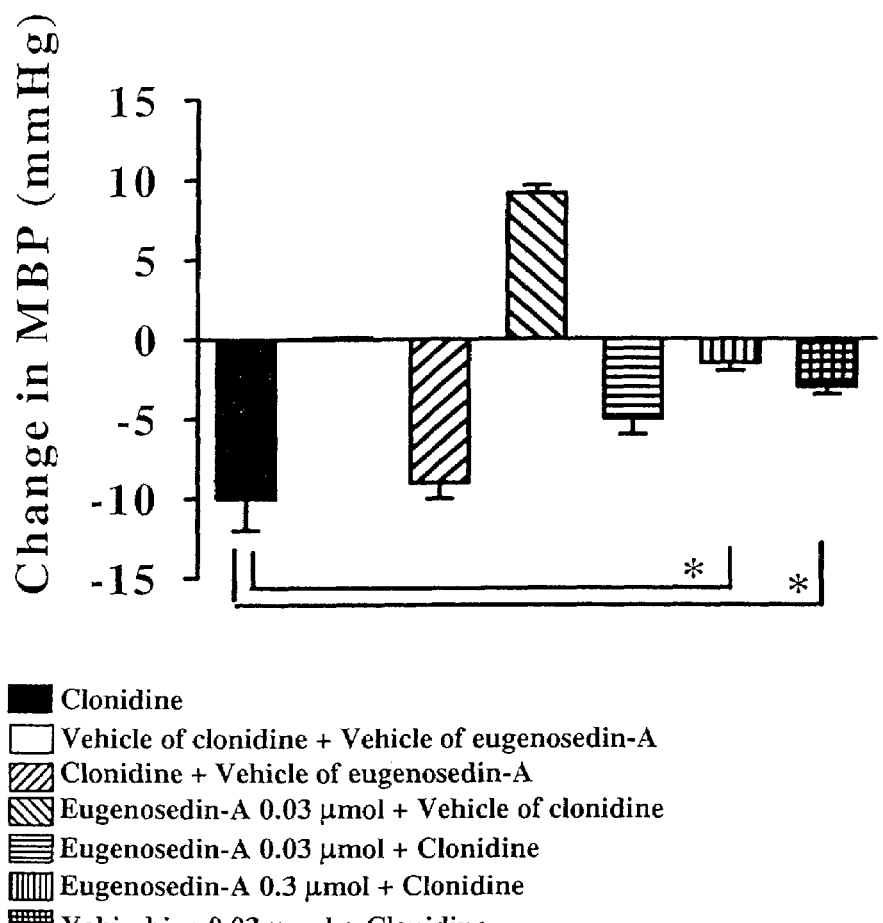

■ Clonidine
□ Vehicle of clonidine + Vehicle of eugenosedin-A
▨ Clonidine + Vehicle of eugenosedin-A
▧ Eugenosedin-A 0.03 μmol + Vehicle of clonidine
▤ Eugenosedin-A 0.03 μmol + Clonidine
▥ Eugenosedin-A 0.3 μmol + Clonidine
▦ Yohimbine 0.03 μmol + Clonidine Means ± S.E., n = 8.
*Significantly different from clonidine treatment group, p < 0.05 [two-way repeated-measures analysis variance (ANOVA)

Figure 3C

Means ± S.E., n = 8.

*Significantly different from clonidine treatment group, $p < 0.05$
[two-way repeated-measures analysis of variance (ANOVA)

Means ± S.E., n = 8. ** Yohimbine induced changes of MBP and HR were significantly different from that of vehicle group, $p < 0.01$; * changes induced by various agents were significantly different from that of vehicle at indicated time, $p < 0.05$ [two-way repeated-measures analysis of variance (ANOVA) followed by Student-Newman-Keuls test.].

Means ± S.E., n = 8. ** Yohimbine induced changes of MBP and HR were significantly different from that of vehicle group, p < 0.01; * changes induced by various agents were significantly different from that of vehicle at indicated time, p < 0.05 [two-way repeated-measures analysis of variance (ANOVA) followed by Student-Newman-Keuls test.]

1. -●- control, 2. -o- $10^{-8}$ M,
3. -▼- $10^{-7}$ M, 4. -▽- $10^{-6}$ M

Cumulative concentration-response curves for noradrenaline were determined on isolated Wistar rat thoracic aortic rings. Each value represents the mean ± S.E., n = 8. *Significantly different from control, p < 0.05 [two-way repeated-measures analysis of variance (ANOVA) followed by Student-Newman-Keuls test.].

1. -●- control,  2. -o- $10^{-8}$ M,
3. -▼- $10^{-7}$ M,  4. -▽- $10^{-6}$ M

Cumulative concentration-response curves for clonidinee were determined on isolated Wistar rat thoracic aortic rings. Each value represents the mean ± S.E., n = 8. *Significantly different from control, $p < 0.05$ [two-way repeated-measures analysis of variance (ANOVA) followed by Student-Newman-Keuls test.].

1. -●- control,  2. -o- $10^{-8}$ M,
3. -▼- $10^{-7}$ M,  4. -▽- $10^{-6}$ M

Cumulative concentration-response curves for serotonin were determined on isolated Wistar rat thoracic aortic rings. Each value represents the mean ± S.E., n = 8. *Significantly different from control, p < 0.05 [two-way repeated-measures analysis of variance (ANOVA) followed by Student-Newman-Keuls test.].

1. -●- control,
2. -o- $10^{-8}$ M,
3. -▼- $10^{-7}$ M,
4. -▽- $10^{-6}$ M

Cumulative concentration-response curves for serotonin were determined on isolated Wistar rat thoracic aortic rings. Each value represents the mean ± S.E., n = 8. *Significantly different from control, p < 0.05 [two-way repeated-measures analysis of variance (ANOVA) followed by Student-Newman-Keuls test.].

a. 5 % alcohol
b. eugenosedin-A 0.1 μM
c. eugenosedin-A 1 μM
d. eugenosedin-A 10 μM Fluorescence intensity of B-phycoerythrin was measured with 540 nm excitation and 575 nm emission.
The moment eugenosedin-A was added to the reaction mixture is indicated by the arrow.
Representative tracings of four independent experiments are shown. Student-Newman-Keuls test.].

1. LPS (10 mg kg$^{-1}$, i.v.); 2. Eugenosedine A (1 mg kg$^{-1}$, i.v.). Arrows indicate the time of application of tested agents. Closed triangle symbol indicates the trace of BP and HR at 1 hr, 3 hr and 5 hr, respectively.

Each point represents the mean of eight rats.
*Significantly different from control, $p < 0.05$ [two-way repeated- measures analysis of variance (ANOVA) followed by Student-Newman-Keuls test.].

3 hours

- ☐ Vehicle
- ■ LPS
- ▨ Eugenosedin-A + LPS
- ▧ Yohimbine + LPS
- ▨ Trazodone + LPS
- ▤ Aminoguanidine + LPS
- ▥ Ascorbic acid + LPS Each point represents the mean of eight rats.
*Significantly different from control, $p < 0.05$ [two-way repeated-measures analysis of variance (ANOVA) followed by Dunnett's test].

5 hours

☐ Vehicle
■ LPS
▨ Eugenosedin-A + LPS
▧ Yohimbine + LPS
▩ Trazodone + LPS
▤ Aminoguanidine + LPS
▥ Ascorbic acid + LPS Each point represents the mean of eight rats.
*Significantly different from control, p < 0.05 [two-way repeated- measures analysis of variance (ANOVA) followed by Dunnett's test].

Each point represents the mean of eight rats.
*Significantly different from control, p < 0.05 [two-way repeated- measures analysis of variance (ANOVA) followed by Dunnett's test].

Each point represents the mean of eight rats.
*Significantly different from control, $p < 0.05$ [two-way repeated-measures analysis of variance (ANOVA) followed by Dunnett's test].

3 hours

- Vehicle
- LPS
- Eugenosedin-A + LPS
- Yohimbine + LPS
- Trazodone + LPS
- Aminoguanidine + LPS
- Ascorbic acid + LPS Each point represents the mean of eight rats.
*Significantly different from control, $p < 0.05$ [two-way repeated-measures analysis of variance (ANOVA) followed by Dunnett's test].

TNF-α (pg/ml)

■ Vehicle
▨ LPS
▧ Eugenosedin-A + LPS
▩ Yohimbine + LPS
☰ Trazodone + LPS
▥ Aminoguanidine + LPS
▦ Ascorbic acid + LPS Each point represents the mean of eight rats.
*Significantly different from control, $p < 0.05$ [two-way repeated- measures analysis of variance (ANOVA) followed by Dunnett's test].

Each point represents the mean of eight rats.
*Significantly different from control, p < 0.05 [two-way repeated-measures analysis of variance (ANOVA) followed by Dunnett's test].

5 hours

■ Vehicle
▨ LPS
▧ Eugenosedin-A + LPS
▩ Yohimbine + LPS
☰ Trazodone + LPS
▥ Aminoguanidine + LPS
▦ Ascorbic acid + LPS Each point represents the mean of eight rats.
*Significantly different from control, p < 0.05 [two-way repeated- measures analysis of variance (ANOVA) followed by Dunnett's test].

LPS (60 mg kg$^{-1}$) was injected (i.p.) into LPS-treated groups.
Three different doses (0.5, 1, 5 mg kg$^{-1}$) were injected 5 min after LPS injection in each group (n = 10).

EUGENOSEDIN-A BASED PHARMACOLIGICAL AGENTS

BACKGROUND OF THE INVENTION

Summary of the Invention

This invention relates to pharmacologically active isoeugenol derivative compounds with $\alpha_2$-adrenergic/5-$HT_{2A}$ antagonist, 5-HT re-uptake inhibition, and antioxidant capabilities. This invention also relates to a method for the manufacture of these compounds.

1. Field of the Invention

Serotonergic and adrenergic receptors, function reciprocally in the central nervous and cardiovascular systems, and are involved in the pharmacologic activities of some antidepressants. It is well established that noradrenaline neurons modulate the activity of the 5-HT (serotonin) system and several lines of evidence support the theory that the 5-HT system influences brain noradrenaline neurons (Villalobos-Molina R, et al., *Eur. J. Pharmacol.*, 277:181–185,1995). Indeed, some selective or subtype-selective $\alpha_2$-adrenoceptor blockers, such as yohimbine, rauwolscine, and phentolamine, have been shown to possess affinity for 5-$HT_{1A}$ receptors in the rat brain (Llado et al., 1996). Although $\alpha_2$-adrenoceptor blockers may provide some protection in rats against bacterial LPS-induced hyperglycemia, tumor necrosis factor-$\alpha$TNF-$\alpha$), interleukin-6 (IL-6), corticosteroid release, and mortality (Haskó G. et al., *J. Endocrinol.*, 144:457–462,1995; Hirata Y. and Ishimaru S., *Clin. Sci.*, 103:332S–335S, 2002), similar protective functions provided by antidepressants with $\alpha_2$-adrenoceptor and 5-HT blocking activities have not been investigated as thoroughly.

Lipopolysaccharide (LPS)-induced inflammatory cytokines, including tumor necrosis factor-$\alpha$ (TNF-$\alpha$), interleukin-1 (IL-1), and interferon (IFN), could be regulated by blocking $\alpha_2$-adrenergic receptors, which are involved in the balance between noradrenergic and serotonergic systems in central neurons (Shen Y. et al., *Life. Sci.*, 65:1773–1786, 1999). Despite the importance of LPS in inflammation, many aspects of LPS-induced dysfunction remain poorly understood. To date, the relationship between LPS-induced hypotension and high mortality is unresolved. LPS is known to affect cerebral neurotransmission. The ability of $\alpha_2$-adrenoceptor blocking antidepressant treatment to attenuate LPS-induced-depression in rats has been cited as evidence that inflammatory cytokines play an important role in depression (Koyama, S. *Am. J. Physiol.*, 16:R665–R662, 1984). Dunn A J. and Swiergiel A H., *Neuroimmonomodulat.*, 9:163–169, 2001). It has been reported that selective blocking of $\alpha_2$-adrenoceptors located on noradrenergic axon terminals resulted in an increase in the release of noradrenaline (Haskó et al., 1995). In in vivo, $\alpha_2$- and $\beta$-adrenoceptors on macrophages can be activated by the endogenous ligand noradrenaline, released from noradrenergic varicosities and by adrenergic drugs. It is suggested that these increases regulate LPS-induced production of cytokines (Szelenyi J, Kiss J P and Vizi E S., *J. Immunol.*, 103:34–40, 2000).

2. Description of the Prior Art

2-Chlorphenyl-1-piperazinyl benzene (CPB) (FIG. 1) is a basic chemical structure, found in trazodone-like antidepressants with $\alpha_2$-adrenoceptor and 5-HT antagonist activities. Some $\beta$-adrenoceptor blockers, such as pindolol, have been found to have nanomolar binding affinities for $^5$-$HT_{1A}$ receptors and have prevented some 5-$HT_{1A}$ receptor-mediated responses (Haddjeri N, de Montigny C, and Blier P., *Biol. Psychiat.*, 45:1163–1169, 1999). $\beta$-adrenergic blocking agents with serotonergic properties have proved beneficial to depressed patients, notably those with myocardial infarction and congestive heart failure (Pitzalis M V. et al., *Am. Heart. J.*, 141:765–771, 2001); Valuck R J. et al., *Dr. S.*, 10:511–516, 2001; Ko D T. et al., *JAMA.*, 288:351–357, 2002). Aryloxypropanolamines [and] especially those which are isoeugenol-based [ones] have been reported to have anti-oxidizing activities in addition to their $\beta$-adrenoceptor blocking effects (Aubriot S.et al., *Bioorgan. Med. Chem.*, 12:209–212, 1995); Huang Y C. et al., *Drug. Dev. Res.*, 47:77–89, 2001). Trazodone, a well known antidepressant, with 5-HT agonist/antagonist activity, 5-HT reuptake inhibition and adrenoceptor blocking activities, was taken as a reference to evaluate associated pharmacologic activities (Cohn et al., 1983; Owens M J.et al., *J. Pharmac. Exp. Ther.*, 283:1305–1322, 1997).

BRIEF DESCRIPTION OF THE DRAWINGS

FIG. 3C illustrates the antagonistic effects of intra-cisternal injections of eugenosedin-A and yohimbine after pretreatment with clonidine on MBP (mean arterial blood pressure).

DESCRIPTION OF THE PREFERRED EMBODIMENTS

The present invention is a set of isoeugenol derivatives with pharmacological attributes including functioning as an $\alpha_2$-adrenergic/5-HT$_{2A}$ antagonist, 5-HT re-uptake inhibitor, as well as antioxidant activities, anti-platelet aggregation, and antiseptic shock activities. The invention also discloses a process for creating some of these compounds.

The compounds shown as Formula 1:

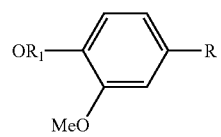

Formula 1 where R present alkyl, and alkenyl;
where R1 present:

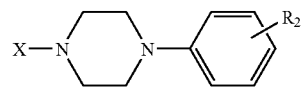

R1 where X present:

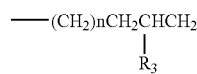

where $R_2$ present halogen (o, m, p), —NH$_2$, —NO$_2$, —CF$_3$, and hydrogen group, select one or ore the one group at o-, m-, or p- position, respectively, on benzene ring; and where $R_3$ present hydrogen group, OH; n present 0 to 2; the said halogen group present F, Cl, Br, I.

To manufacture this combination Epichlorohydrin was mixed with isoeugenol and NaOH dissolved in ethanol and boiled to reflux for 2–6 hours. Ethanol was then removed from the resulting mixture and the mixture was passed through silica gel column eluted with n-hexane and ethyl acetate, and dried with reduced pressure, to obtain 4-epoxy isoeugenol.

The 4-epoxy isoeugenol was mixed with a solution of piperazine dissolved in methanol and mixed to reflux at 100° C. for 2–6 hours. The obtained mixture was then removed and the included methanol removed by drying at a reduced pressure by utilizing a vacuum pump. The residue was then passed through silica gel column chromatography, eluated with n-hexane and ethyl acetate, dried by reduced pressure, and crystallized with methanol to obtain a white crystal compound.

Figure 1:
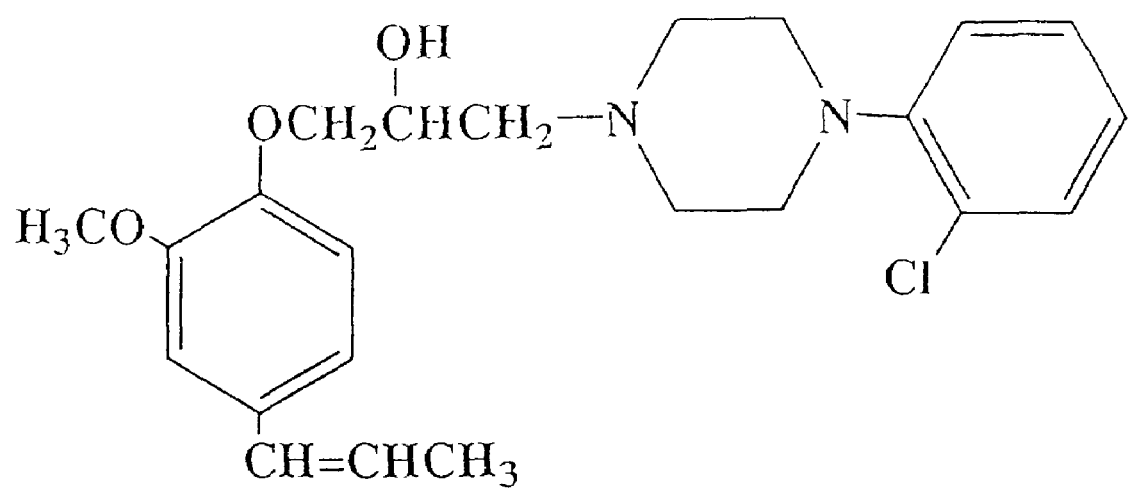
FIG. 1 illustrates eugenosedin-A.

With the view of developing an antidepressant with enhanced anti-oxidizing, $\alpha_2$-adrenoceptor blocking, cytokine inhibiting, and pindolol-like β-adrenoceptor blocking activities, the invention first synthesized eugenosedin-A (2-chlorphenyl-1-1piperazinyl)-propoxy-3-methoxy-1-propylenyl-benzene (FIG. 1) by combining isoeugenol-based oxypropanolamine, and CPB (2-chlorphenyl-1-piperazinyl benzene).

This combination resulted in producing eugenosedin-A, which chemically has an antioxidant oxypropanolamine base, and provides CPB-related $\alpha_2$-adrenoceptor and 5-HT receptor antagonist properties, including inhibition of LPS-induced hypotension, hyperglycemia, and cytokine formation. In the present study, the inventor examined the receptor binding affinity and blockade of 5-HT re-uptake, 5-HT and adrenergic receptor inhibition, antioxidant, peroxyl radical scavenging, and cardiovascular responses regulated by eugenosedin-A in the CNS (central nervous systems). Particularly, the inventor emphasized the inhibitory activities of eugenosedin-A, compared with those of antidepressant trazodone, on LPS-induced hypotension, hyperglycemia, and cytokine formation.

Pharmacological activities. The pharmacological activity of this invention has been demonstrated by the following pharmacological experiments:

Animals. Wistar rats were provided from the National Laboratory Animal Breeding and Research Center (Taipei, Taiwan). They were housed under conditions of constant temperature and controlled illumination (light on between 7:30 and 19:30). Food and water were available ad libitum. The study was approved by the Animal Care and Use Committee of Kaohsiung Medical University.

Drugs and chemicals. Yohimbine, 5-nonyloxytryptamine, methylsergide, clonidine, isoprenaline, ketanserin, noradrenaline, serotonin, and aminoguanidine HCl were purchased from Sigma Chemical Co. (St. Louis, Mo., U.S.A.). Trazodone was obtained from Lotus Medical Supply (Taipei). Eugenosedin-A synthesized in this laboratory was solvated in 50% absolute alcohol, 10% propylene glycol and further diluted with distilled water. All of the [$^3$H] ligand was purchased from New England Nuclear Corp. (Boston, Mass., U.S.A.). Nonspecific-ligand (10 μM): serotonin, phentolamine, propanolol and specific [$^3$H]-ligand (nM): WAY100635 (1), GR125743 (3), ketanserin (0.5), prazosin (0.2), yohimbine (2), CGP12177 (1 and 3) were used in the displacement experiment for different types of receptors.

Intravenous injection. The experiments were carried out as previously described (Wu B N. et al., *Biochem. Pharmacol.*, 48:101–109, 1994). In brief, Wistar rats weighing 250–300 grams were anesthetized with pentobarbital sodium (50 mg kg$^{-1}$, i.p.). Following tracheal cannulation, systemic arterial BP and HR were recorded from the femoral artery by a pressure transducer (model P10EZ; Spectramed, Oxnard, Calif., U.S.A.) connected to a recorder (GOULD, Valley View, Ohio, Model P50). Body temperature was maintained at 37° C. by an electric heating pad. A femoral vein was cannulated for intravenous injection of drugs and LPS (10 mg kg$^{-1}$). Pretreatment with eugenosedin-A, yohimbine or trazodone (0.5, 1 mg kg$^{-1}$, i.v.) and aminoguanidine or ascorbic acid (15 mg kg$^{-1}$, i.v.) 15 minutes before LPS injection was followed by recording BP changes 1, 3, and 5 hours after LPS injection.

Figure 2A:
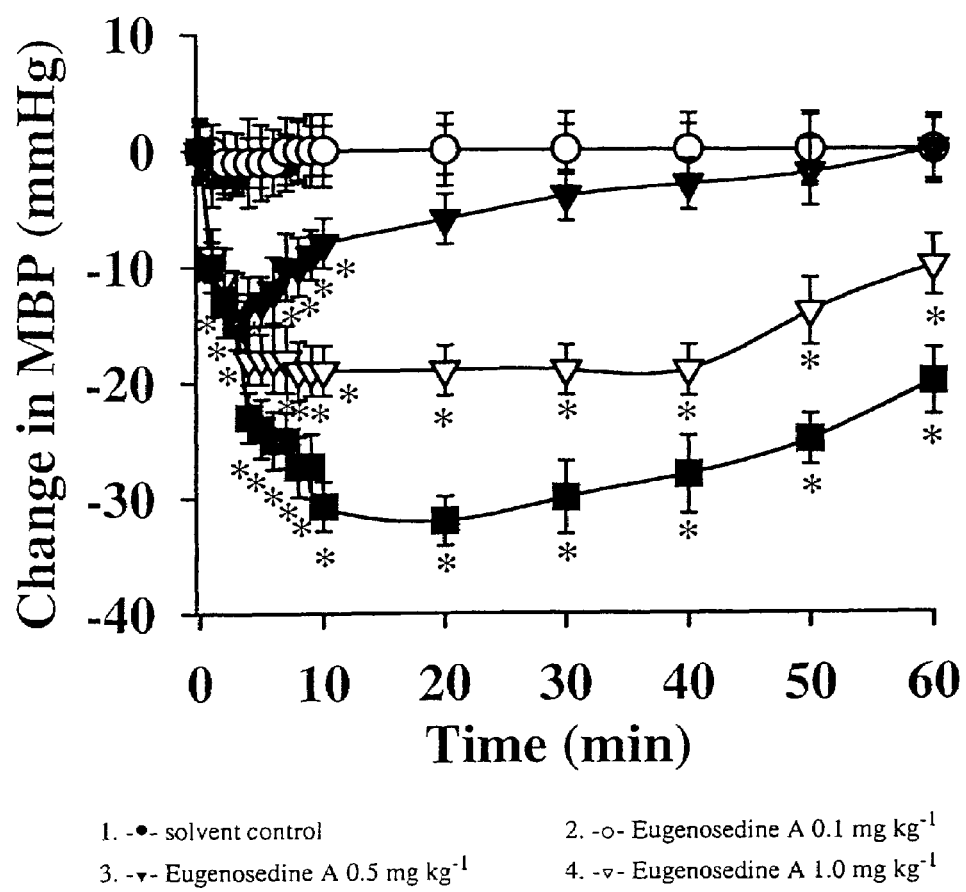
FIG. 2A illustrates the effect of eugenosedin-A on mean arterial blood pressure (MBP) in Wistar rats anesthetized with pentobarbital.
Figure 2B:
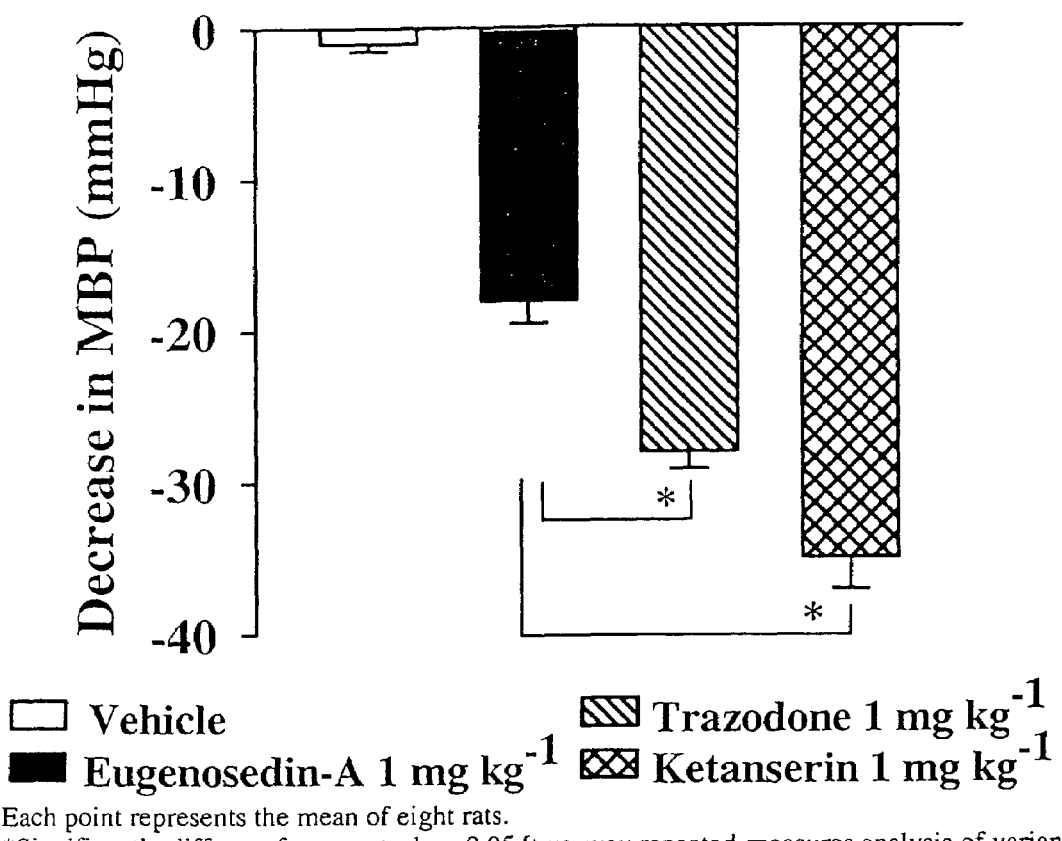
FIG. 2B illustrates the effects of eugenosedin-A, trazodone and ketanserin on mean arterial blood pressure (MBP) in Wistar rats 30 minutes after injection.
Figure 3A:
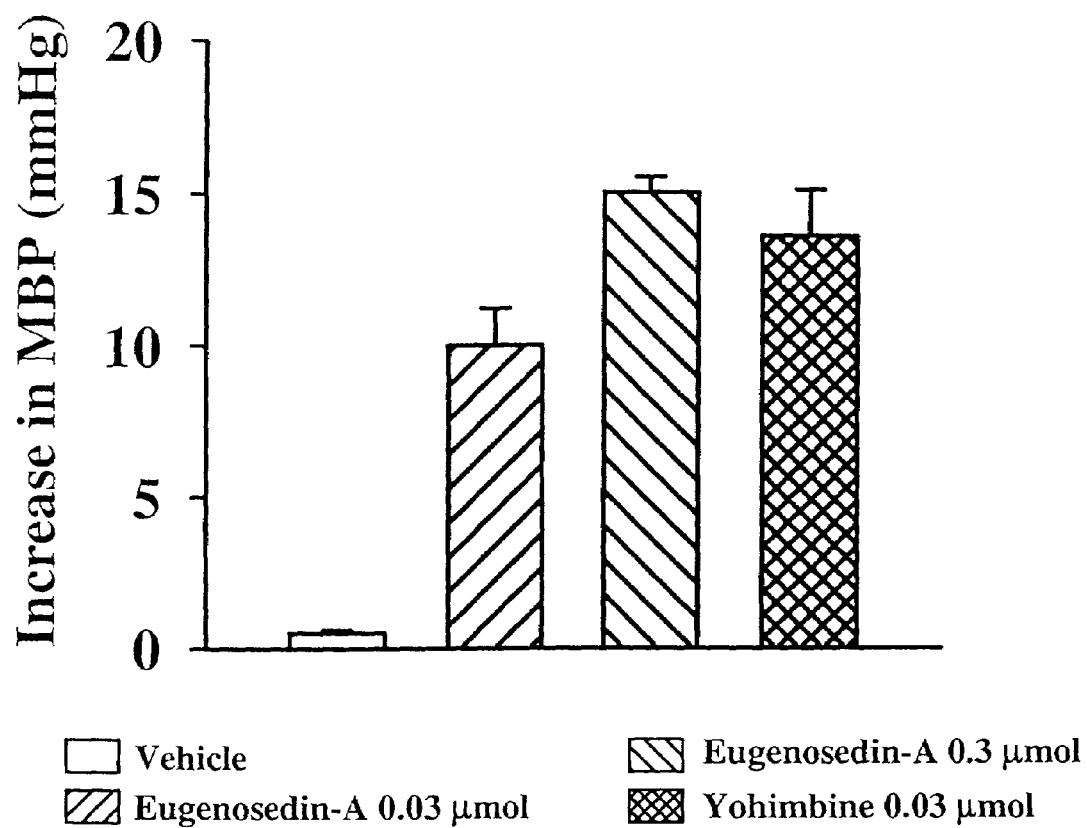
FIG. 3A illustrates the effects of intra-cisternal injections of eugenosedin-A and yohimbine on MBP(mean arterial blood pressure).
Figure 3B:
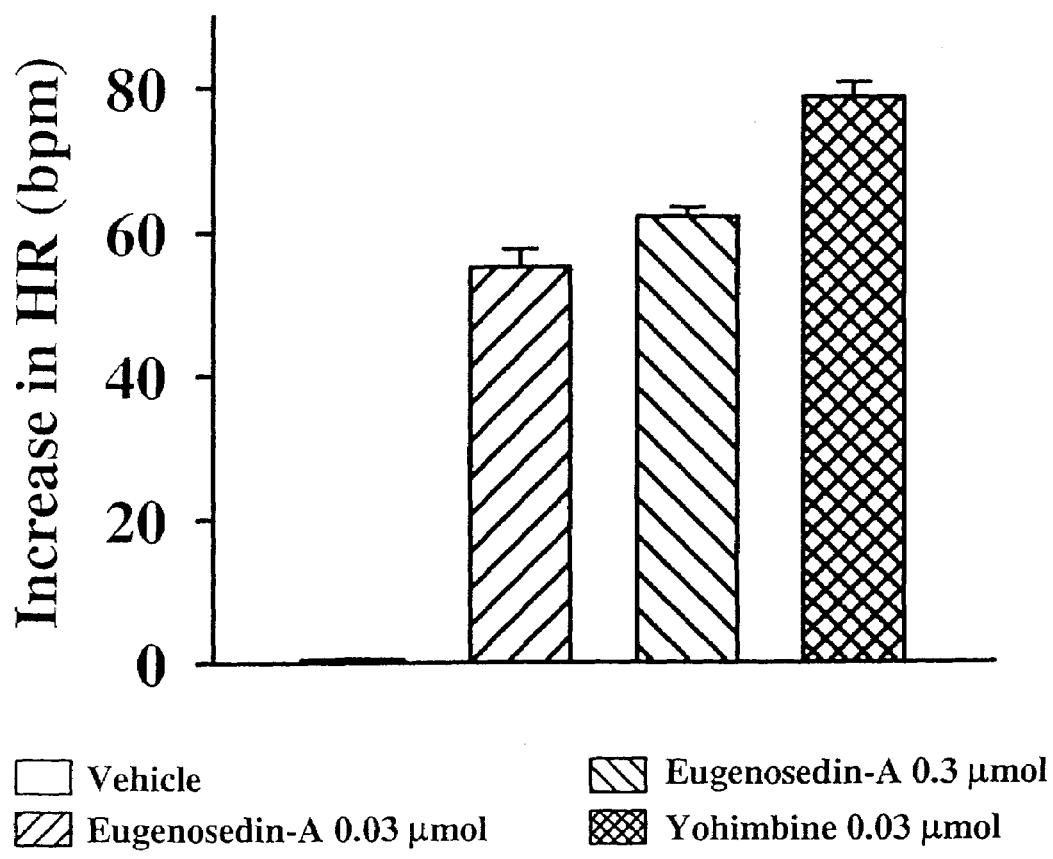
FIG. 3B illustrates the effects of intra-cisternal injections of eugenosedin-A and yohimbine on HR (heart rate).

Depressor and pressor activities. Acute intravenous injection of eugenosedin-A (0.1, 0.5, 1.0 mg kg$^{-1}$) caused mild arterial hypotension in pentobarbital-anesthetized Wistar rats. Eugenosedin-A' depressor effect was less than trazodone and ketanserin, respectively (FIGS. 2A and 2B). Intra-cisternal injections of eugenosedin-A (0.3, 0.03 µmol), trazodone (0.3, 0.03 µmol) and yohimbine (0.03 µmol) increased mean arterial BP (blood pressure) and HR (heart rate) (FIG. 3A). Eugenosedin-A at 0.3 µmol caused mild pressor responses, up to 15 mmHg, and increased the HR up to 60 bpm. Yohimbine at a lower dose of 0.03 µmol also increased pressor responses up to 13 mmHg and the HR up to 78 bpm. In contrast, micro-injection of clonidine (38 pmol) produced long-lasting hypotension (curtailed at 10 mmHg) and HR (curtailed at 18 bpm) in pentobarbital-anesthetized rats. The hypotensive effect of clonidine was antagonized by eugenosedin-A, trazodone, and yohimbine, when they had been administered 15 min before clonidine injection (FIG. 3B). The bradycardic effect of clonidine was reduced by eugenosedin-A at 0.3 µmol. Neither eugenosedin-A nor yohimbine at 0.03 µmol concentrations antagonized the bradycardic effect of clonidine (FIG. 3B).

Figure 4A:
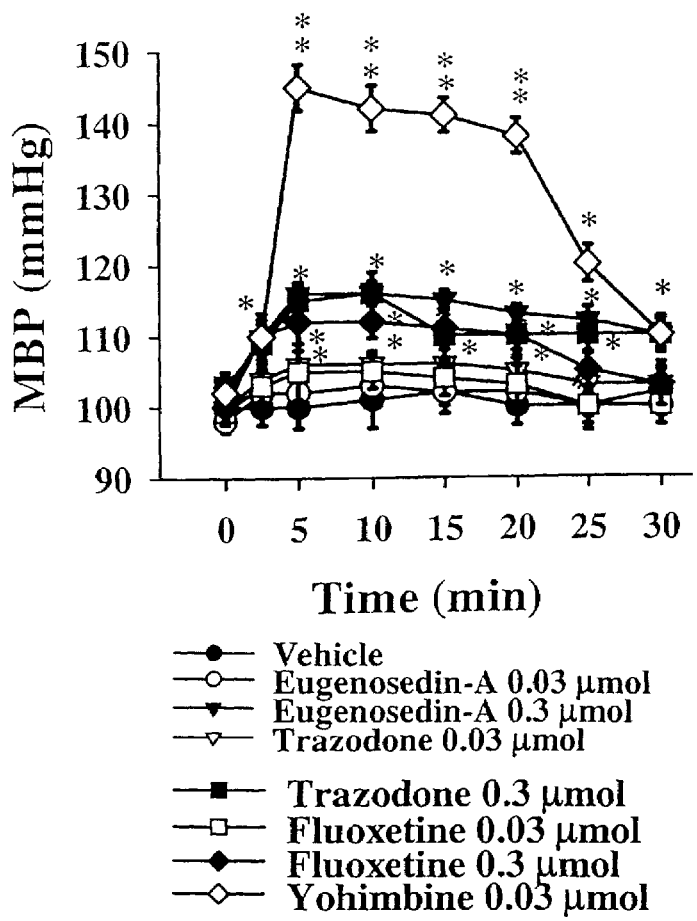
FIG. 4A illustrates BP response of NTS injections of eugenosedin-A, fluoxetine, trazodone and yohimbine in rats for 30 min after injection.

In NTS (nucleus tractus solitarius), both eugenosedin-A, trazodone and fluoxetine (0.03, 0.3 µmol) produced mild pressor responses and increased the HR. At a lower dose of 0.03 µmol, yohimbine, an $\alpha_2$-adrenoceptor blocker, produced a strong pressor response up to 13 mmHg and HR up to 78 bpm, respectively (FIGS. 4A and 4B).

Figure 5A:
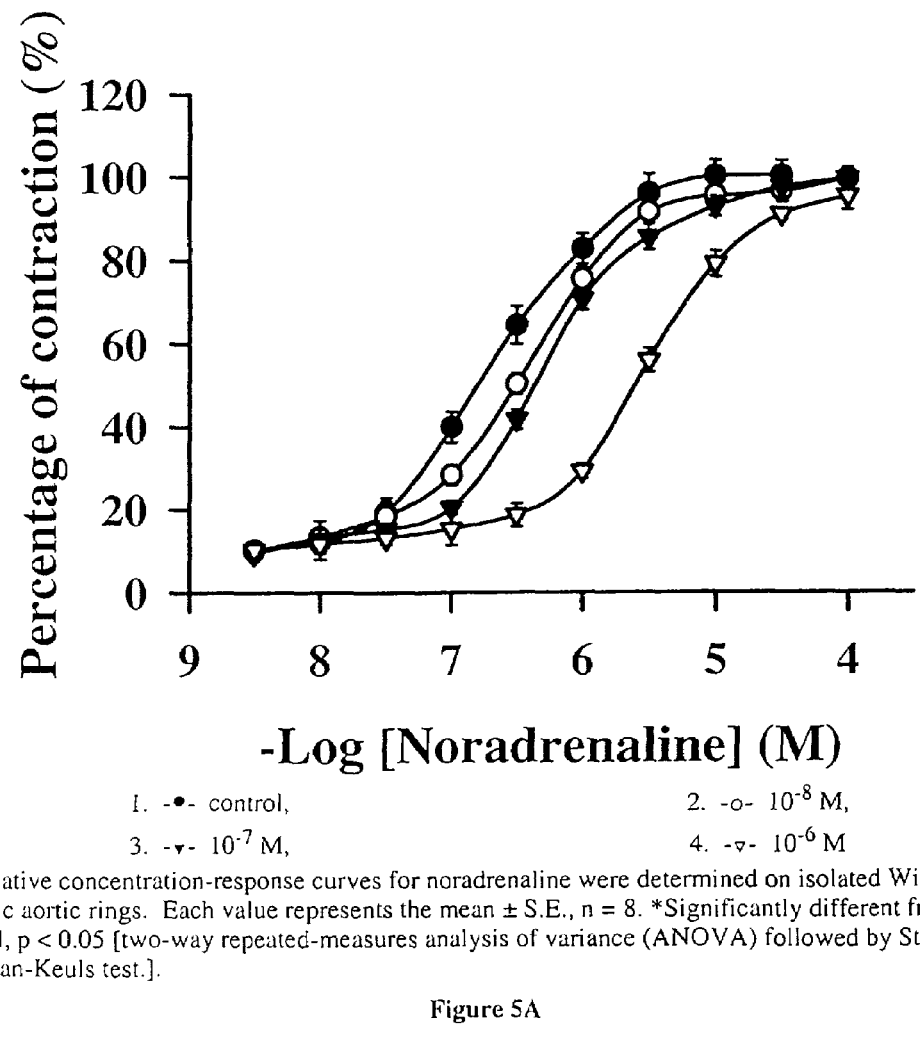
FIG. 5A illustrates the antagonism of noradrenaline-induced vasocontractility by eugenosedin-A on thoracic aorta.
Figure 5B:
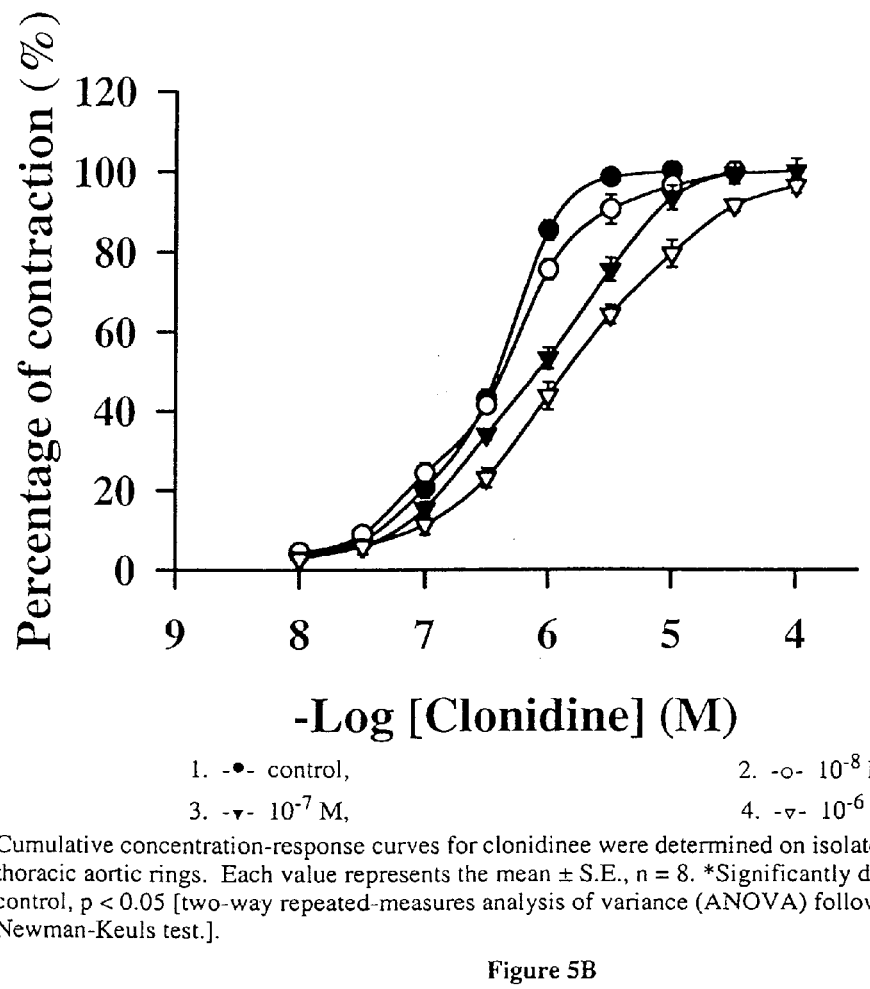
FIG. 5B Antagonism of clonidine-induced vasocontractility by eugenosedin-A on thoracic aorta.
Figure 5C:
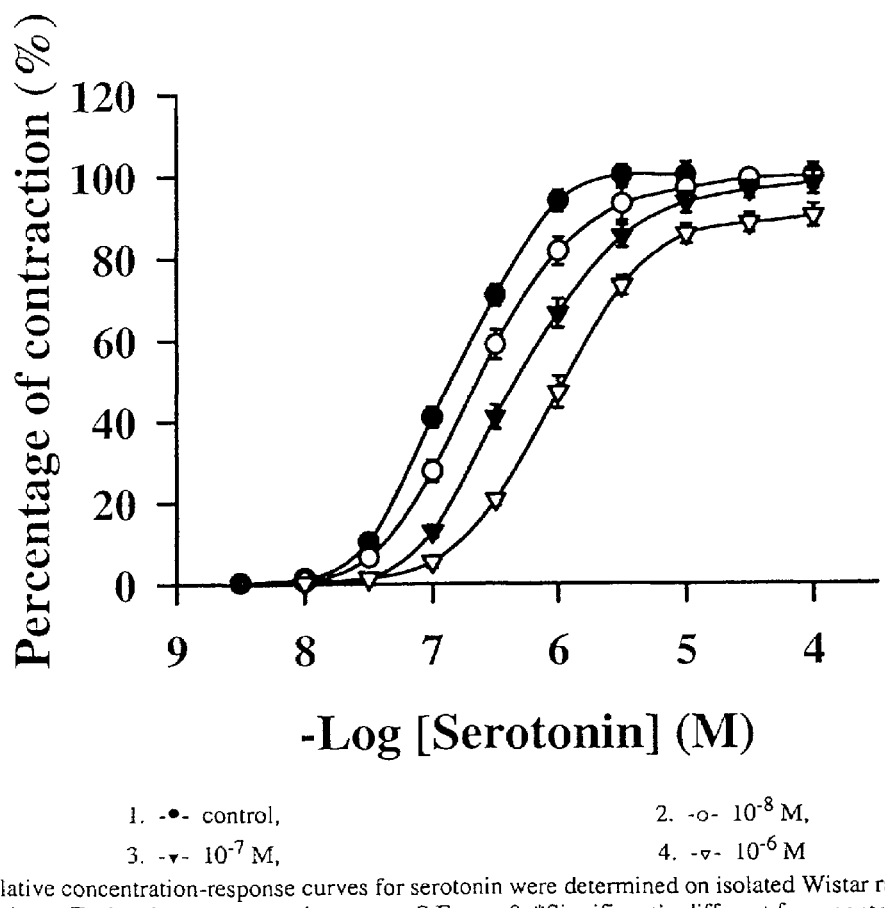
FIG. 5C Antagonism of serotonin-induced vasocontractility by eugenosedin-A on thoracic aorta.
Figure 5D:
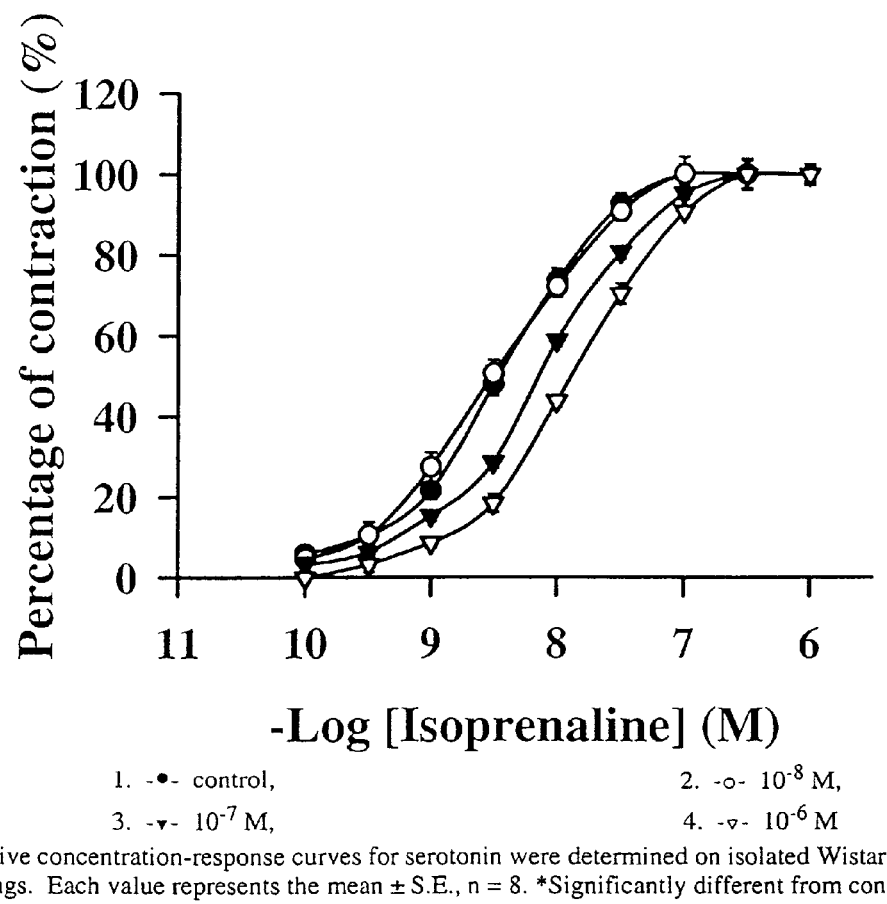
FIG. 5D illustrates the antagonism of isoprenaline-induced contractility by eugenosedin-A on left atria.

Adrenergic receptor antagonist activities. Eugenosedin-A ($10^{-8}$, $10^{-7}$, $10^{-6}$ M) competitively inhibited cumulative noradrenaline- and clonidine-induced contractile activities, causing a dose-dependent parallel shift to the right of the noradrenaline and clonidine concentration-response curves in isolated rat thoracic aorta (FIGS. 5A and 5B). Regarding $\beta_1$-adrenoceptor blocking activity in electrically stimulated left atria, eugenosedin-A ($10^{-8}$, $10^{-7}$, $10^{-6}$ M) concentration-dependently inhibited cumulative isoprenaline-induced positive inotropic effects and produced a dose-dependent parallel shift to the right of isoprenaline-induced concentration-response curves in isolated rat left atria (FIG. 5D).

5-HT$_{2A}$ receptor antagonist activity. Eugenosedin-A ($10^{-8}$, $10^{-7}$, $10^{-6}$ M) concentration-dependently inhibited cumulatively added 5-HT-induced contractile activities in isolated rat thoracic aortas. Concentration-response curves of 5-HT were dose-dependently parallel-shifted to the right by eugenosedin-A (FIG. 5C). Other β-adrenoceptor blockers had no influence on the contractile response to 5-HT.

Receptor binding activity. In this invention, eugenosedin-A, propranolol, prazosin, ketanserin, methylsergide and 5-HT all produced competitive binding activity with [$^3$H] GR125743 (5-HT$_{1B/1D}$) and, [$^3$H]ketanserin (5-HT$_{2A}$) on serotonergic receptors in rat cortex, with [$^3$H]prazosin on $\alpha_1$ receptors in rat cortex, with [$^3$H]yohimbine on $\alpha_2$ receptors in rat cortex, with [$^3$H]CGP-12177 on $\beta_1$ receptors in rat ventricle, and with [$^3$H]CGP-12177 on $\beta_2$ receptors in rat lung. Eugenosedin-A had a higher binding affinity than other β-adrenergic antagonists for 5-HT$_{2A}$ receptors. The order of potency on 5-HT$_{2A}$ receptors was ketanserin >methylsergide >eugenosedin-A >5-HT >propranolol >prazosin. Methylsergide and 5-HT had lower binding affinities for $\alpha_1$ receptors. The order of $\alpha_1$ receptor binding potency was prazosin >ketanserin >eugenosedin-A >methylsergide, propranolol and 5-HT. Prazosin had strong $\alpha_1$ and $\alpha_2$-adrenoceptor affinities. Ketanserin, methylsergide and eugenosedin-A also had binding affinities for $\alpha_2$-adrenoceptors. The order of $\alpha_2$ receptor binding potency was prazosin >eugenosedin-A >ketanserin >methylsergide >propranolol and 5-HT. Propranolol had high $\beta_1\beta_2$-adrenoceptor-affinity. In striking contrast, eugenosedin-A had lower binding affinity for $\beta_2$-adrenoceptors.

Inhibitory activities of 5-HT re-uptake. The IC$_{50}$ values of 5-HT uptake inhibition by eugenosedin-A and trazodone in rat cortex were 3.426×10$^{-5}$ M and 1.164×10$^{-6}$ M, respectively. Although eugenosedin-A was not as potent as trazodone, it potently inhibited 5-HT cortical uptake.

Antioxidant and peroxyl radical scavenging activities. In order to eliminate the possibility that eugenosedin-A and other test compounds interfered with the assay, the test agents were added directly to MDA (malondialdehyde) standard before the TBA reagent was added.

Figure 10:
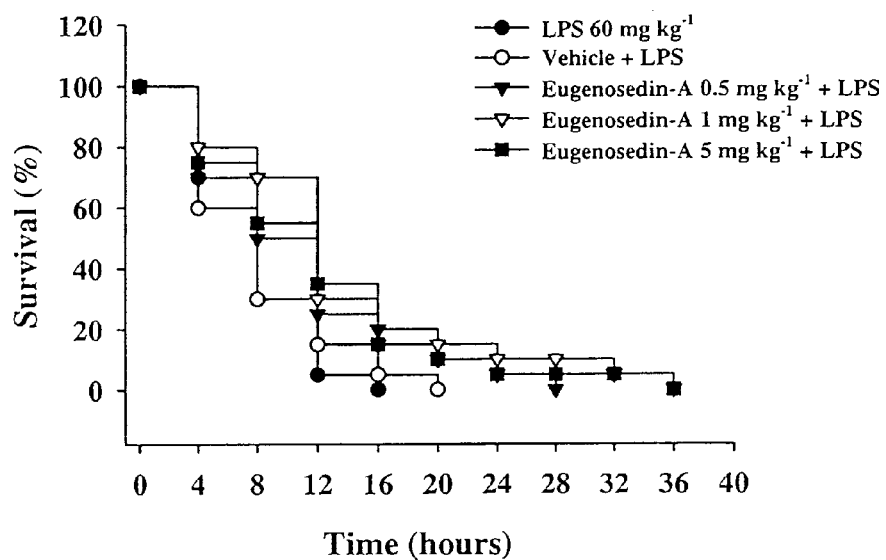
FIG. 10 illustrates the effect of eugenosedin-A on the survival rate of LPS-treated ddk mice.

Exposure of B-phycoerythrin to AAPH (2,2'-Azobis(2-amidinopropane) dihydrochloride)-derived aqueous peroxyl radicals induced a transient decay of the fluorescent intensity. Eugenosedin-A produced a concentration dependent decrement of the fluorescence loss and prolongation of the lag time (FIG. 10). But yohimbine and trazodone could not scavenge the peroxyl radical in experiments.

Figure 7:
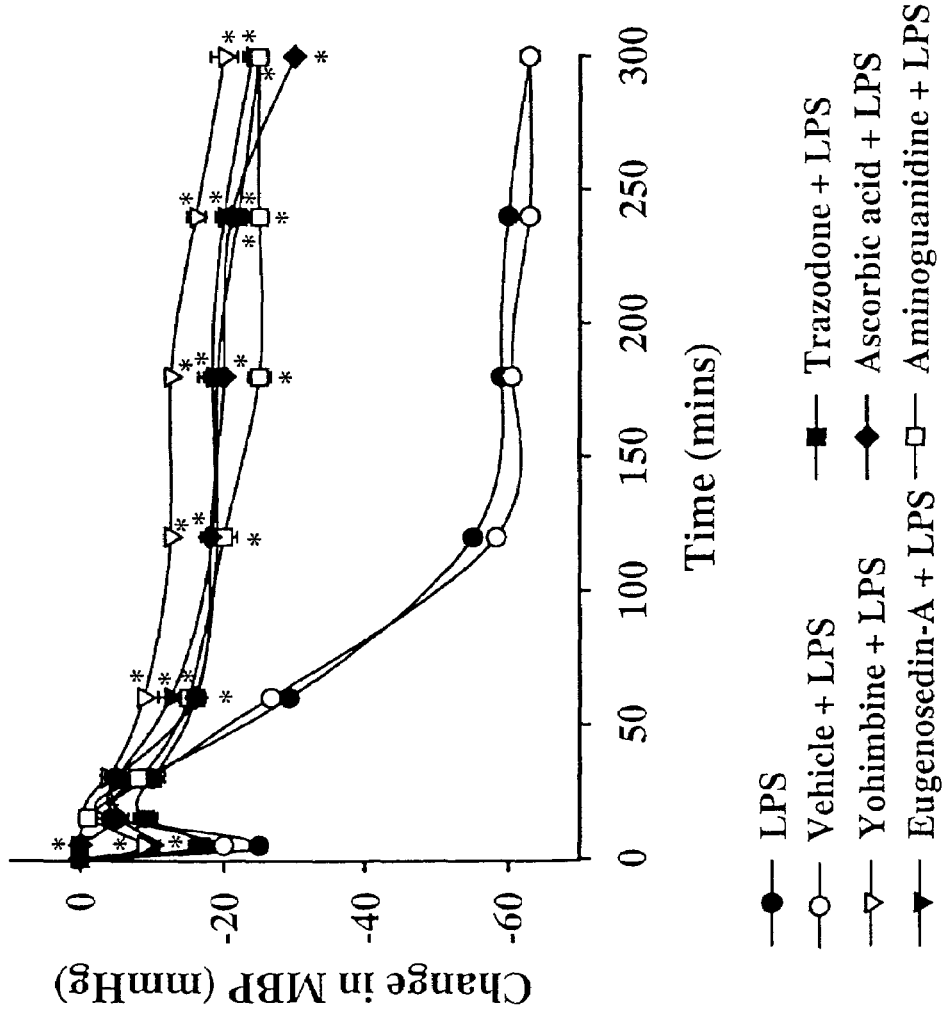
FIG. 7 illustrates the recording of normalization effect of eugenosedin-A on LPS-induced hypotension in rats anesthetized with pentobarbital.
Figure 8A:
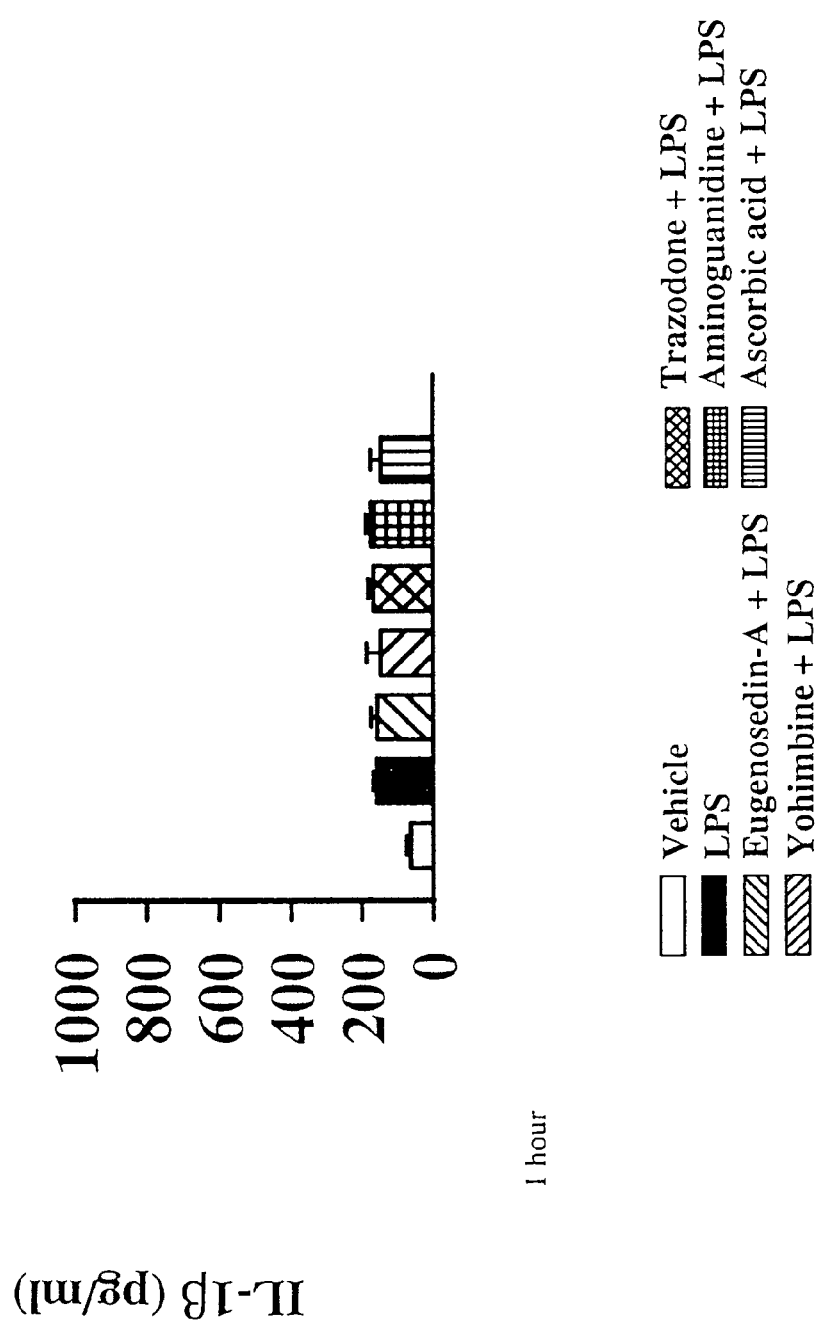
FIG. 8A illustrates Eugenosedin-A decreased levels of IL-1$\beta$ when LPS was injected into Wistar rats anesthetized with pentobarbital.
Figure 8B:
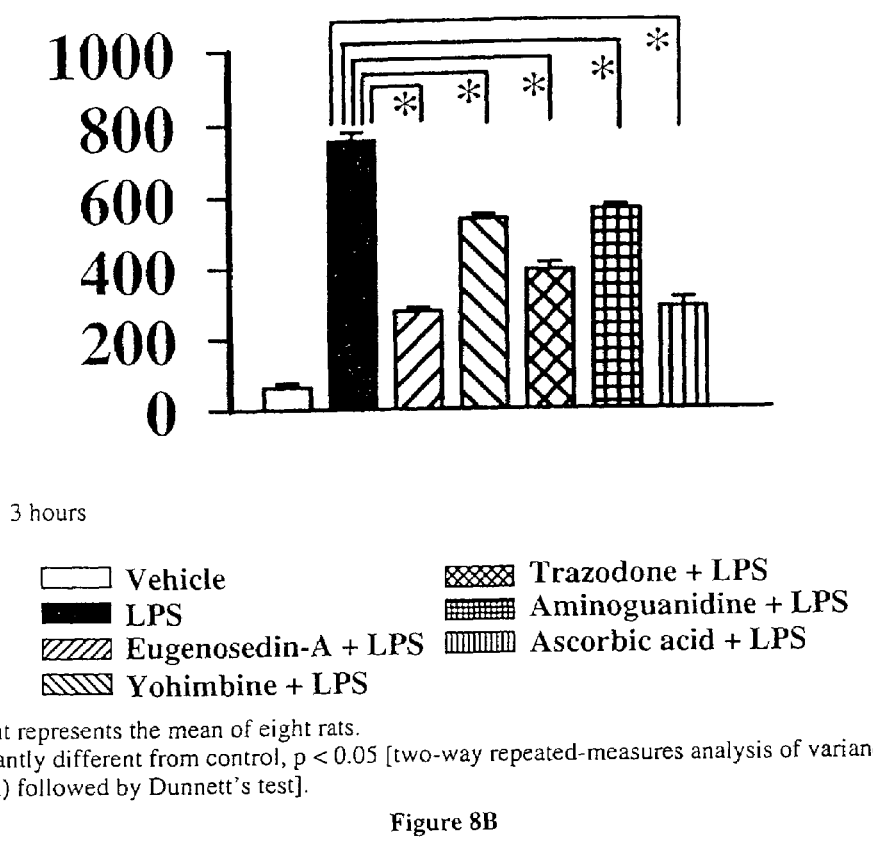
FIG. 8B illustrates Eugenosedin-A decreased levels of IL-1$\beta$ when LPS was injected into Wistar rats anesthetized with pentobarbital.
Figure 8C:
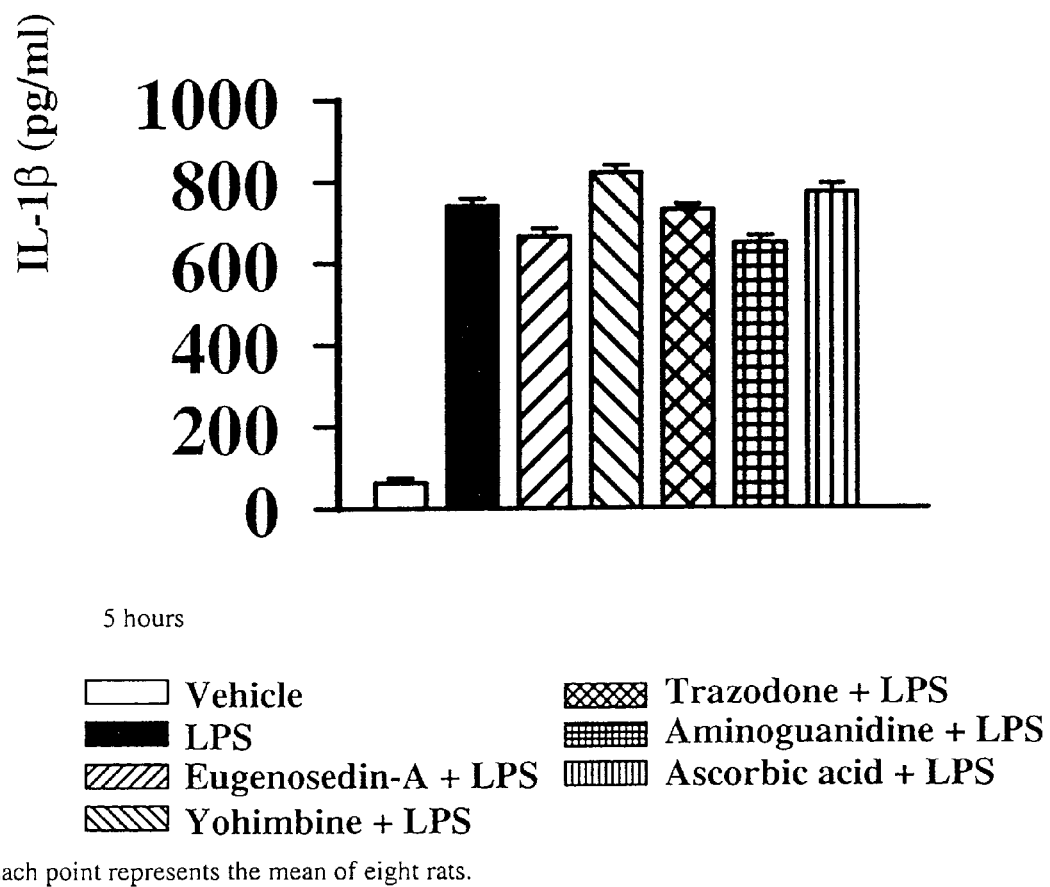
FIG. 8C illustrates Eugenosedin-A decreased levels of IL-1β when LPS was injected into Wistar rats anesthetized with pentobarbital.
Figure 8D:
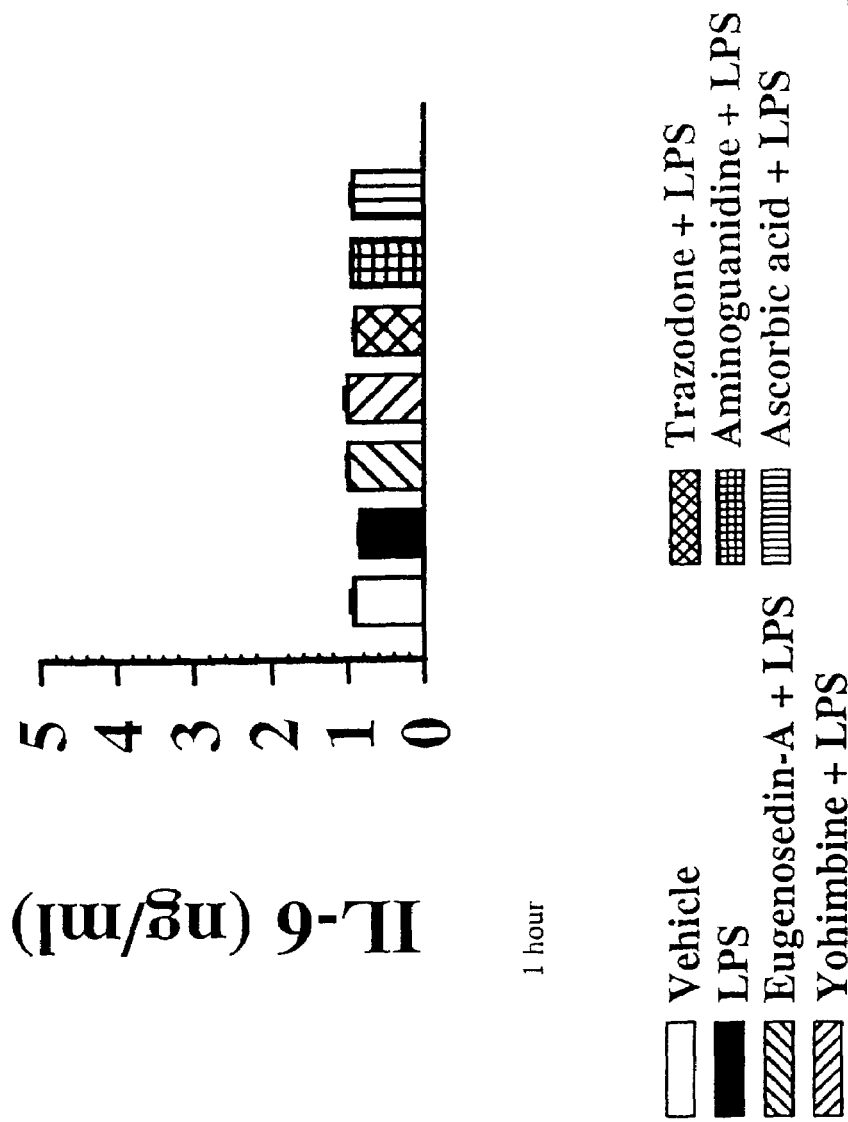
FIGS. 8D, 8E, and 8F illustrate Eugenosedin-A decreased levels of IL-6 when LPS was injected into Wistar rats anesthetized with pentobarbital.
Figure 8E:
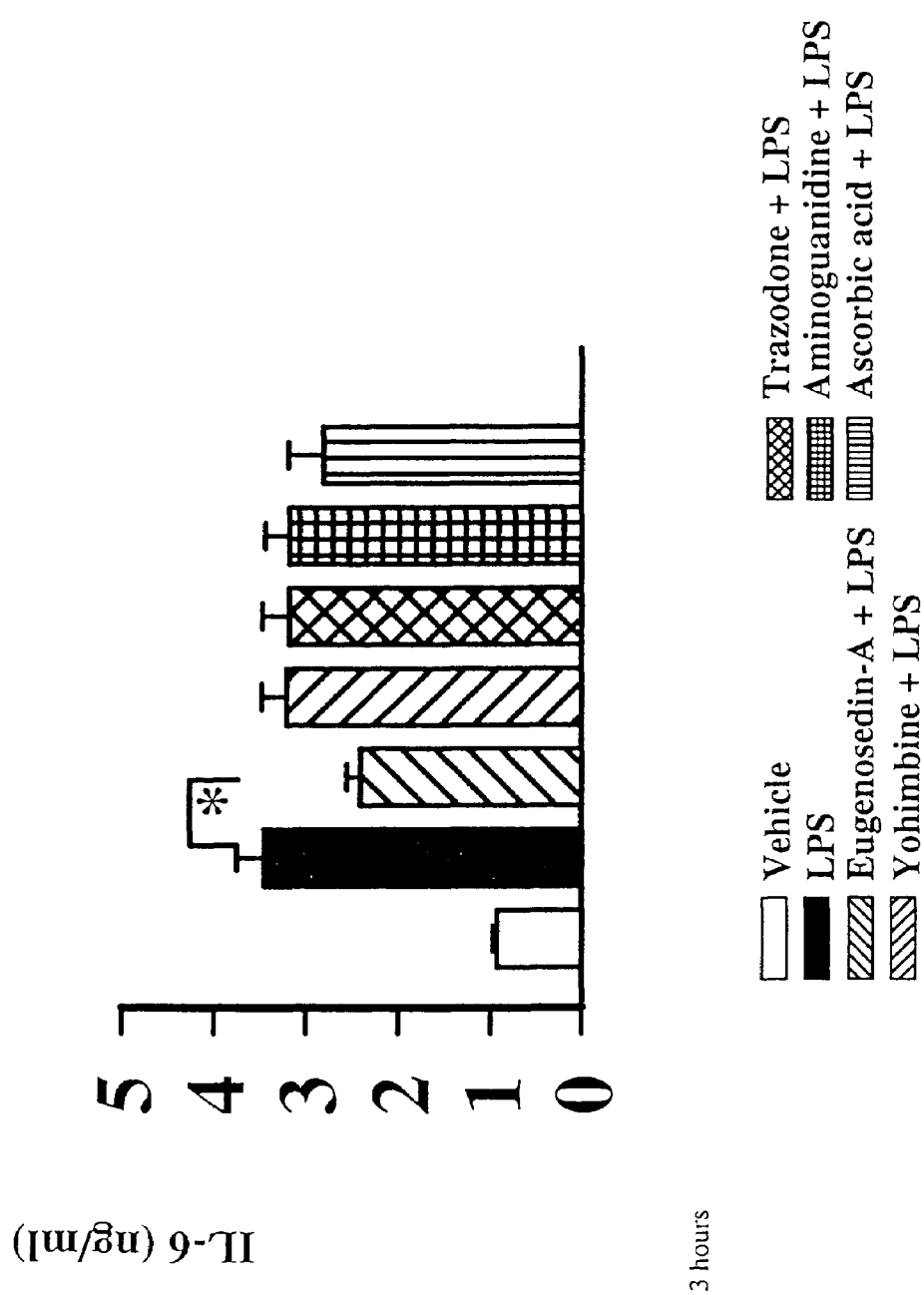
Figure 8F:
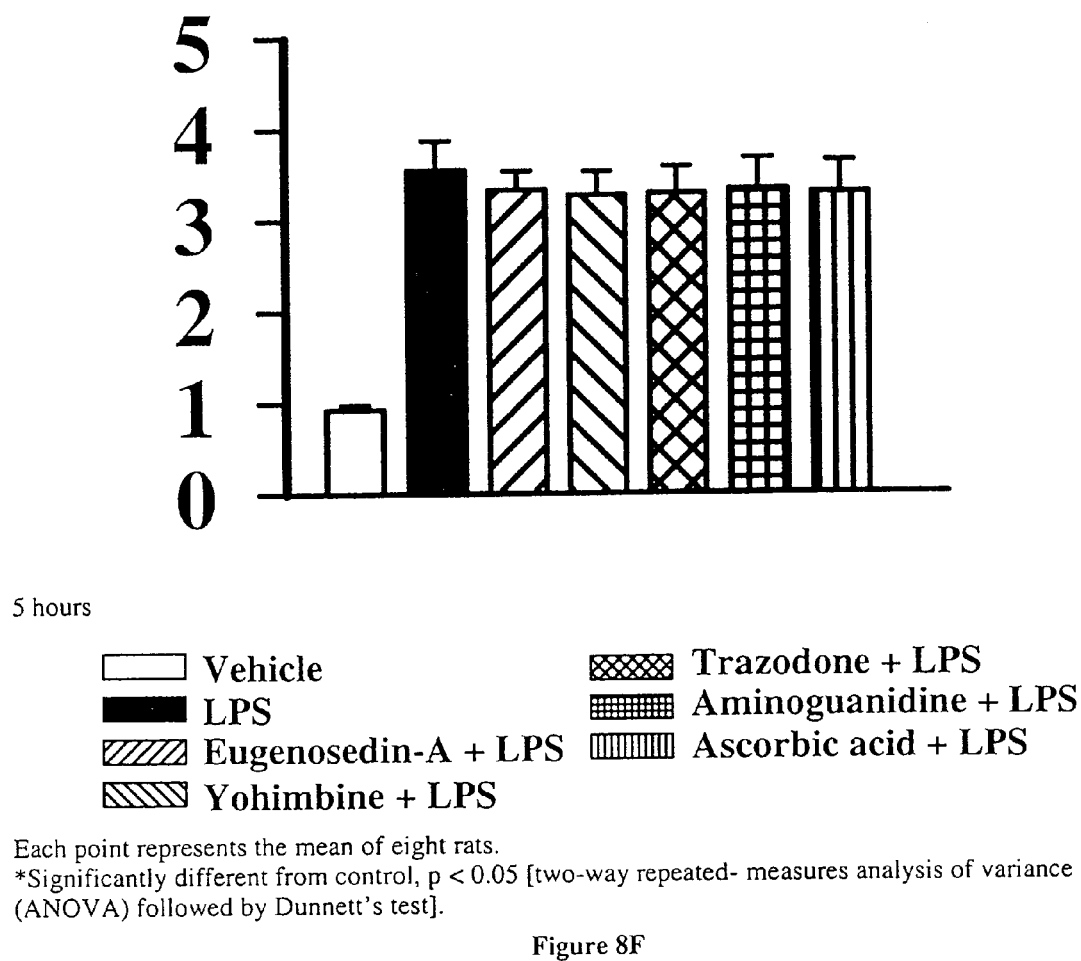
Figure 8G:
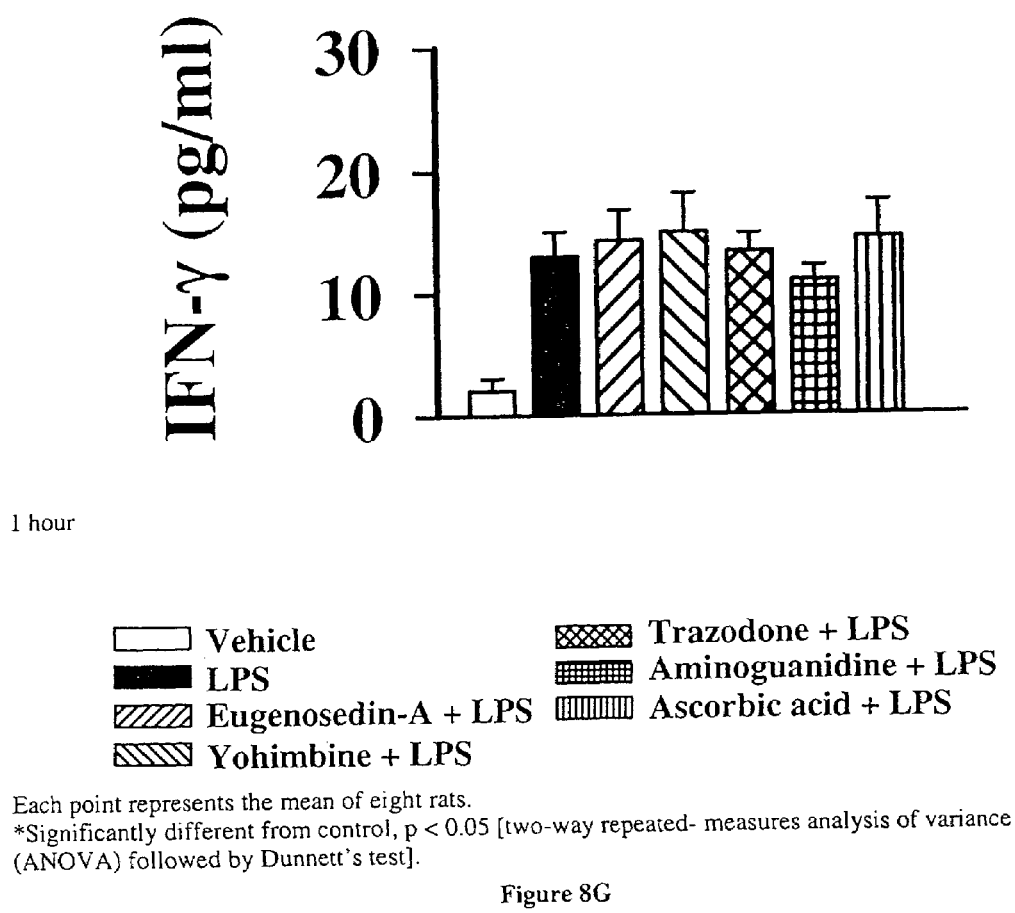
FIG. 8G illustrates Eugenosedin-A decreased levels of IFN-γ when LPS was injected into Wistar rats anesthetized with pentobarbital.
Figure 8H:
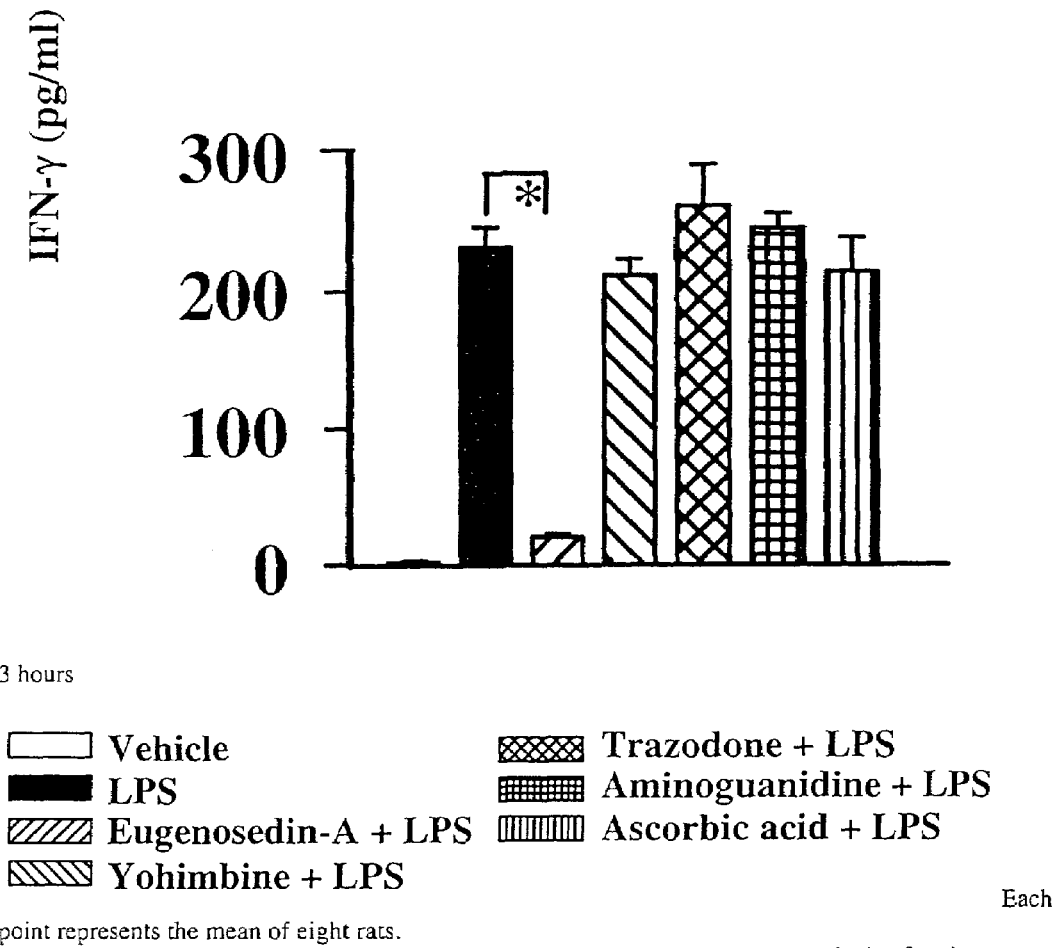
FIG. 8H illustrates Eugenosedin-A decreased levels of IFN-γ when LPS was injected into Wistar rats anesthetized with pentobarbital.
Figure 8I:
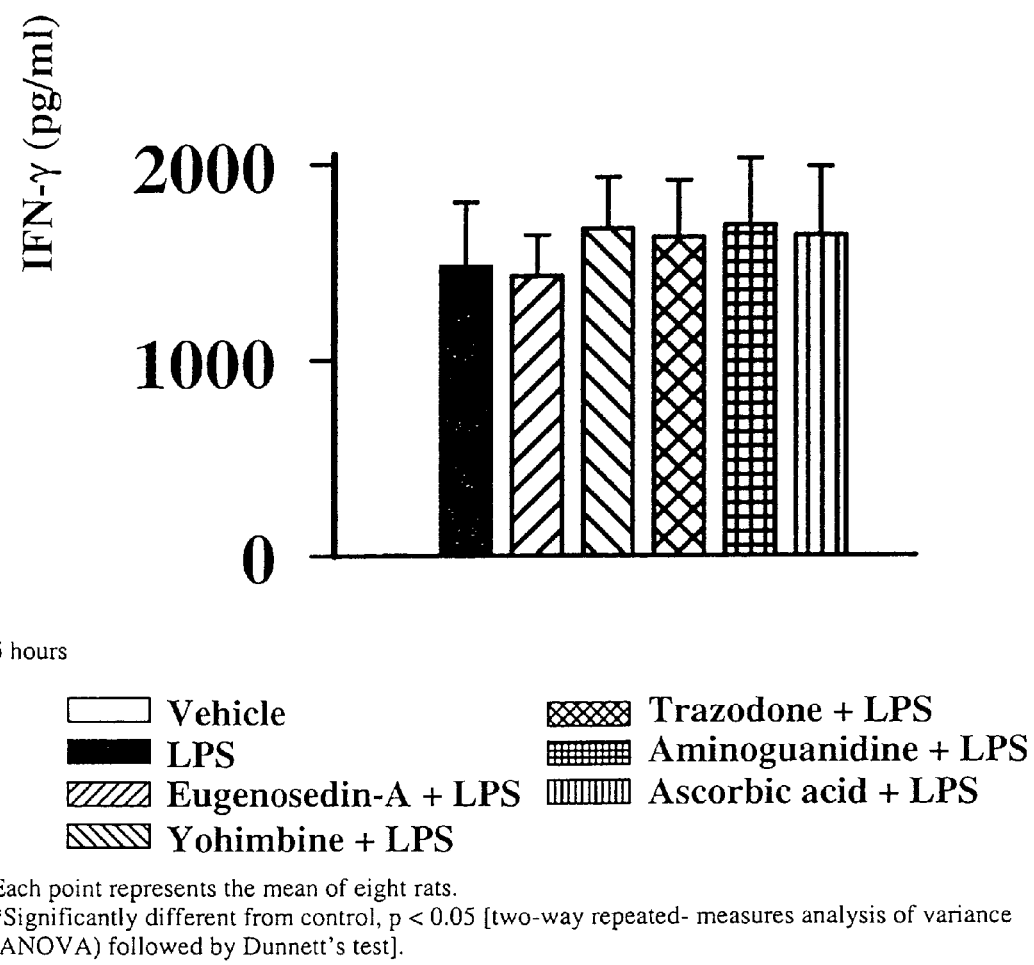
FIG. 8I illustrates Eugenosedin-A decreased levels of IFN-γ when LPS was injected into Wistar rats anesthetized with pentobarbital.
Figure 8J:
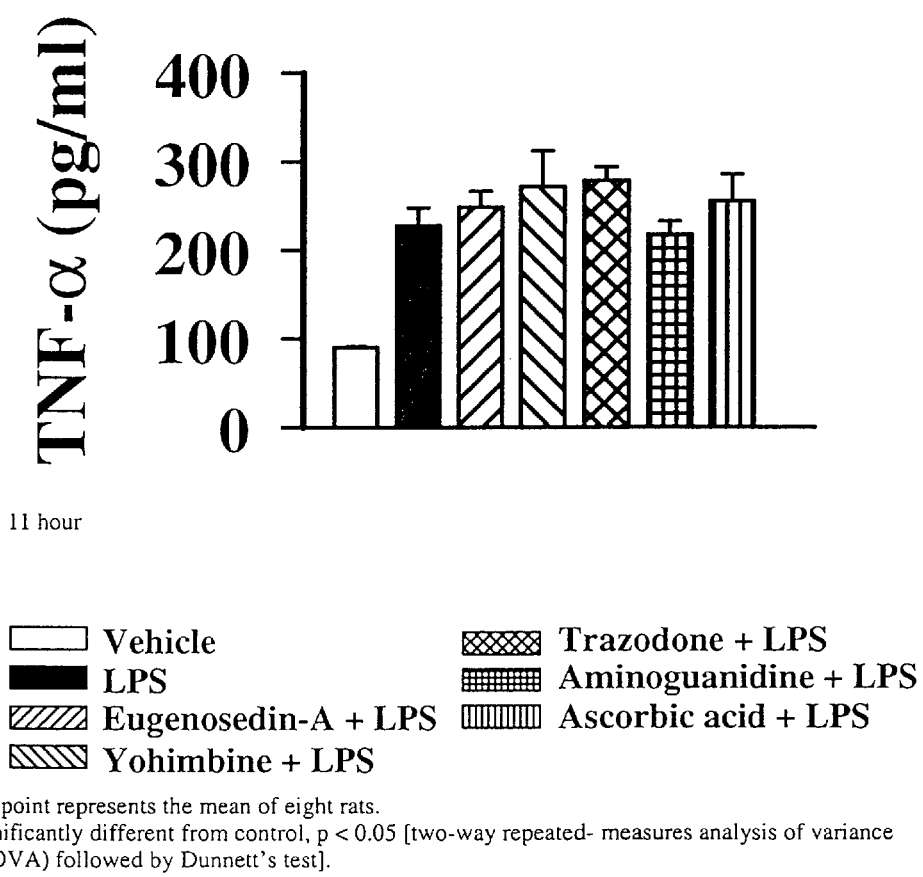
FIG. 8J illustrates Eugenosedin-A decreased levels of IFN-γ when LPS was injected into Wistar rats anesthetized with pentobarbital.
Figure 8K:
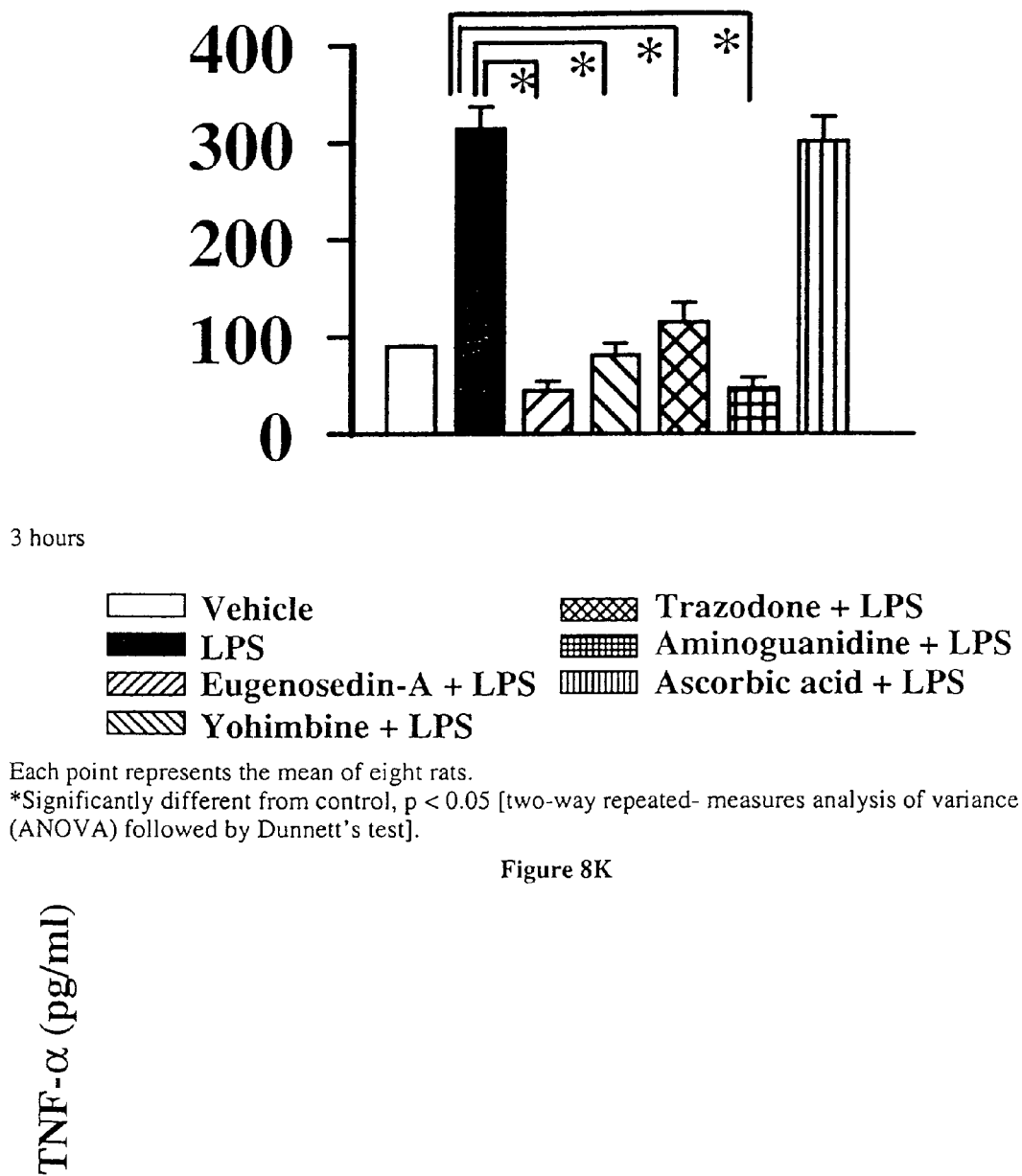
FIG. 8K illustrates Eugenosedin-A decreased levels of IFN-γ when LPS was injected into Wistar rats anesthetized with pentobarbital.
Figure 8L:
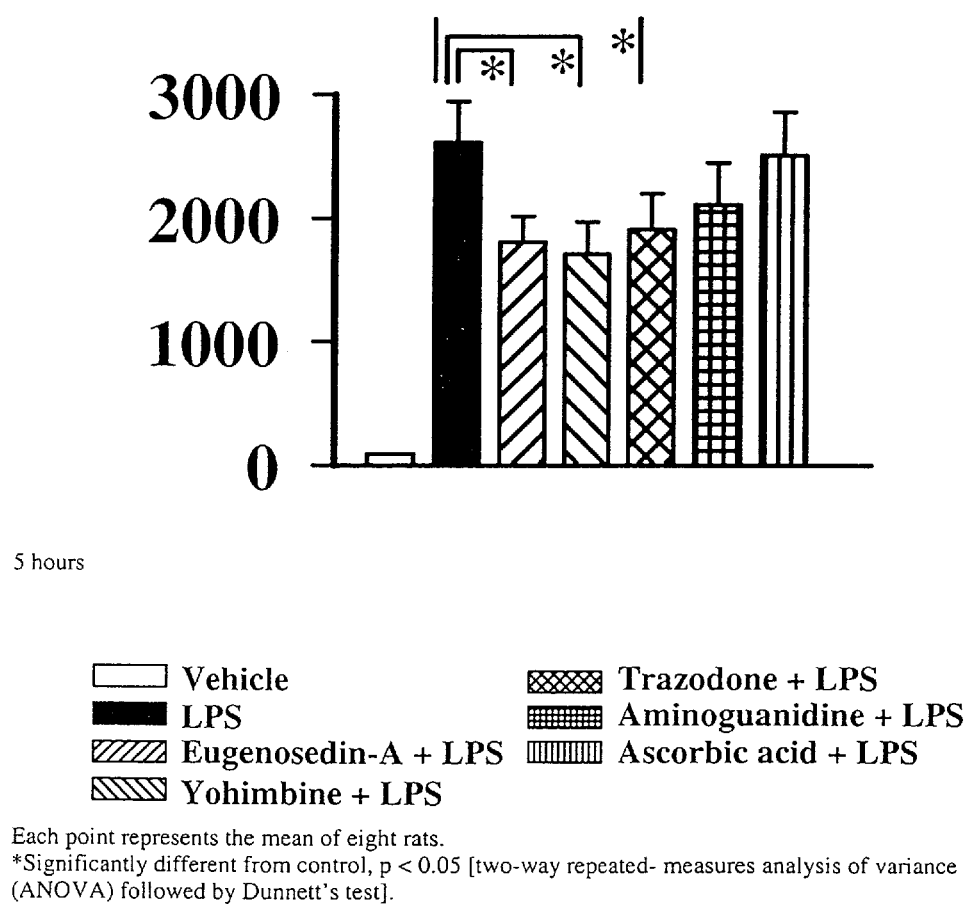
FIG. 8L illustrates Eugenosedin-A decreased levels of IFN-γ when LPS was injected into Wistar rats anesthetized with pentobarbital.

Inhibition on LPS-induced hypotension. A single injection of LPS (10 mg kg$^{-1}$, i.v.) produced biphasic hypotension, an immediate and transient decrease in BP, which was followed by partial recovery within 15 minutes, and then followed by prolonged hypotension. The first hypotensive phase was not affected by Pretreatment with eugenosedin-A, yohimbine and trazodone (0.5 mg kg$^{-1}$, i.v.) 15 minutes before LPS injection, however, at higher doses (1 mg kg$^{-1}$. i.v.) they exactly attenuated it. All significantly reduced the second prolonged hypotensive phase at doses of 0.5 and 1 mg kg$^{-1}$ (i.v.), respectively. Aminoguanidine and ascorbic acid (15 mg kg$^{-1}$, i.v.) also inhibited LPS-induced hypotension (FIG. 7).

Protective effects on LPS-induced vascular hyporeactivity. The isolated aortas from LPS-treated rats were hyporeactive to phenylephrine (10$^{-8}$~10$^{-4}$ M) in vitro. Intravenous injection of eugenosedin-A (1 mg kg$^{-1}$) before or after application of LPS improved the aortic contractility better than in vehicle group. One hour after administration of LPS, vascular contractility was similar to that of controls. In comparison with yohimbine, trazodone, aminoguanidine and ascorbic acid, eugenosedin-A was more effective in protecting from LPS-induced hyporeactivity of the aorta.

Inhibition of LPS-induced cytokine immunoreactivities and hyperglycemia. As shown in FIG. 7, 3 hours after LPS (10 mg kg$^{-1}$, i.v.) administration, cytokine immunoreactivities of IL-1β, IL-6, IFN-γ and TNF-α were increased. Pretreatment with eugenosedin-A (1 mg kg$^{-1}$, i.v.) significantly inhibited the LPS-induced increase in all of these cytokines, but yohimbine, trazodone, aminoguanidine and ascorbic acid inhibited the increase of IL-1β and TNF-α significantly.

In experiments without LPS injection, blood glucose levels in rats treated with vehicle as control, were not changed. However, LPS injection caused hyperglycemia at 1 and 3 hour, followed by a progressive hypoglycemia at 5 hour. Eugenosedin-A, aminoguanidine and ascorbic acid all inhibited the initial hyperglycemic response to LPS at 1 and 3 hours, but could not reverse the hypoglycemic response at 5 hour (FIG. 8).

Figure 9A:
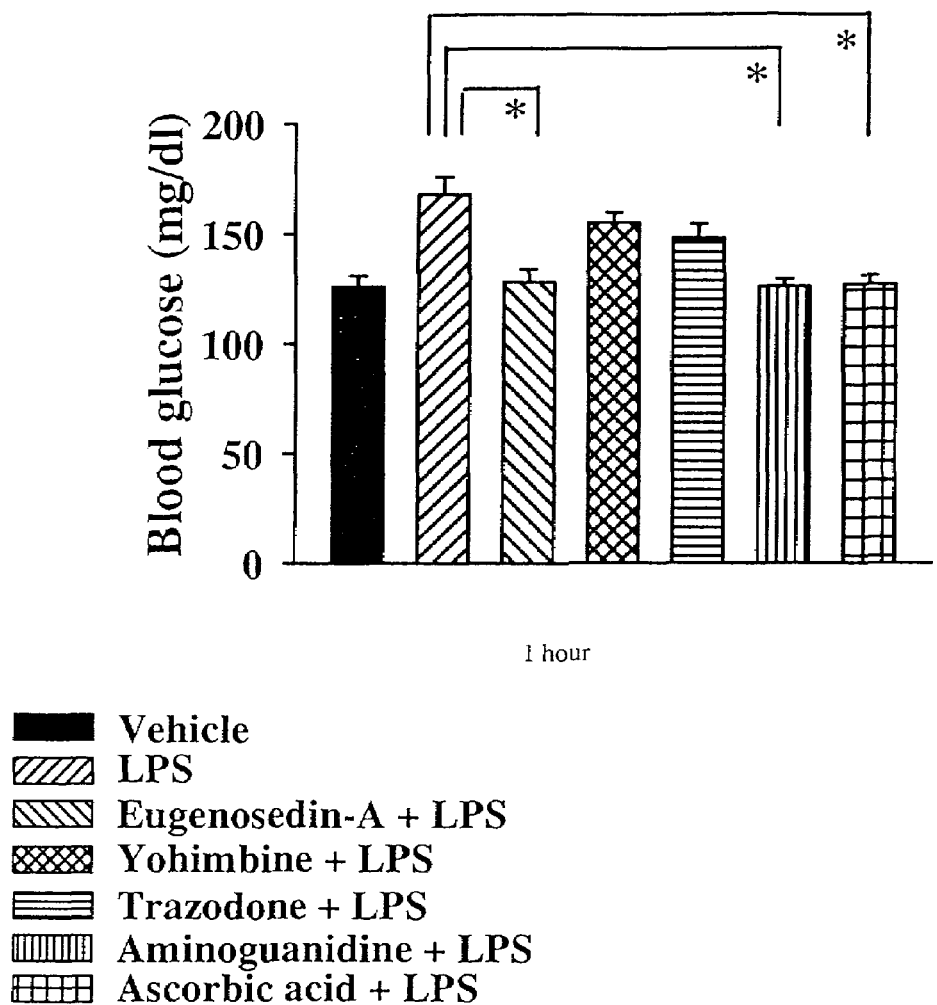
FIG. 9A illustrates 1 hour Eugenosedin-A decreased blood glucose levels after LPS was injected into Wistar rats anesthetized with pentobarbital.
Figure 9B:
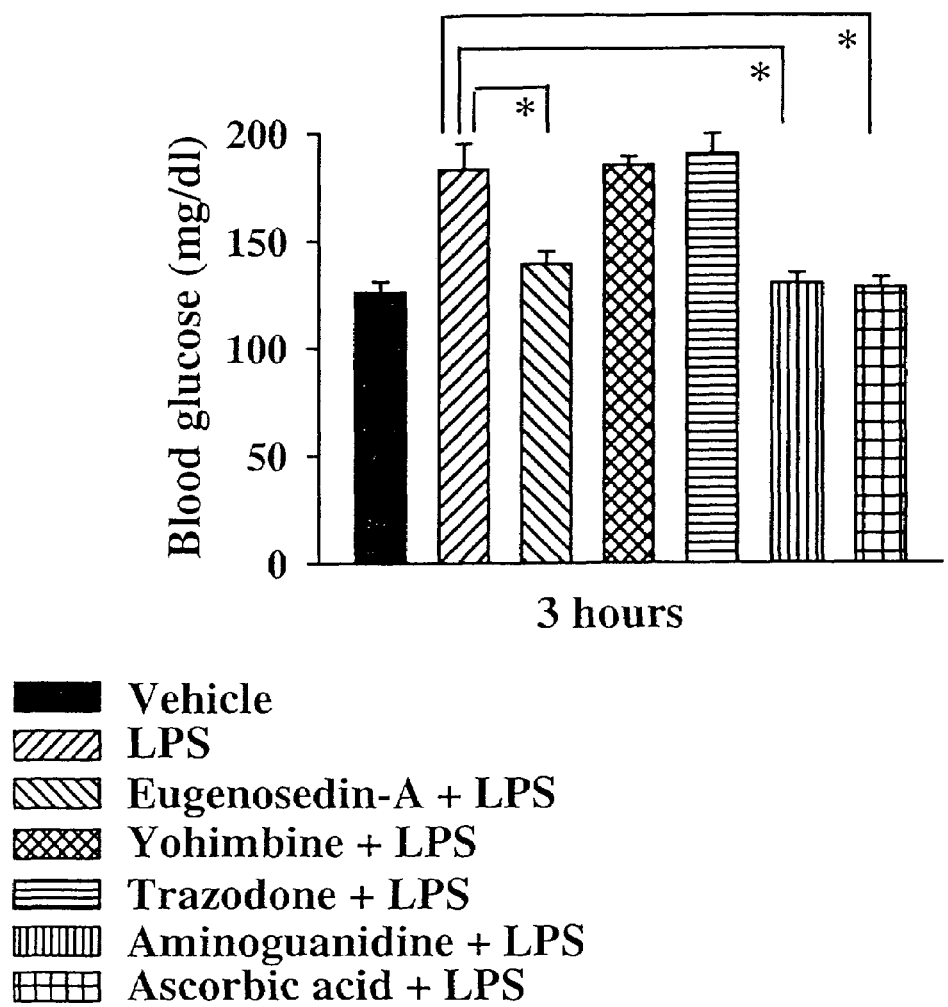
FIG. 9B illustrates 3 hours Eugenosedin-A decreased blood glucose levels after LPS was injected into Wistar rats anesthetized with pentobarbital.
Figure 9C:
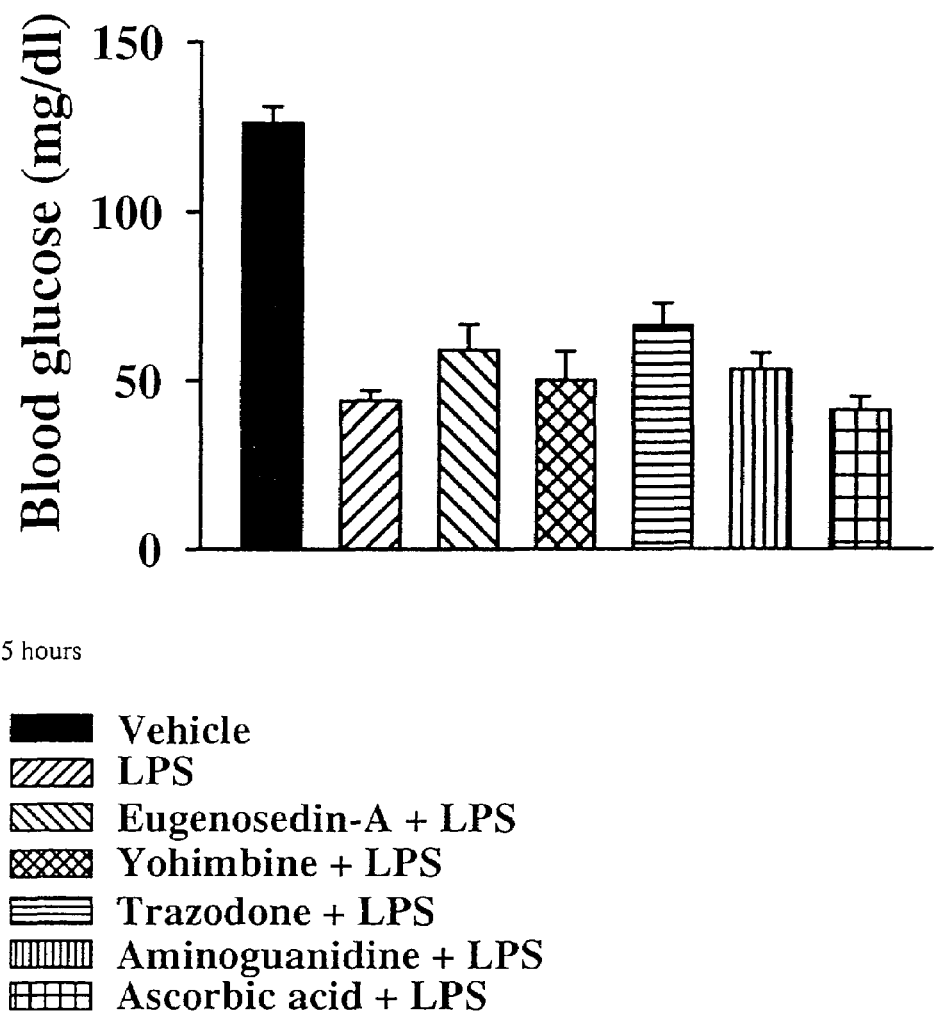
FIG. 9C illustrates 5 hours Eugenosedin-A decreased blood glucose levels after LPS was injected into Wistar rats anesthetized with pentobarbital.

Survival rates. Survival rate 16-hours after intravenous injection of LPS (60 mg kg$^{-1}$, i.p.) was zero. In contrast, Pretreatment with eugenosedin-A (0.5, 1, 5 mg kg$^{-1}$, i.p.) significantly increased the survival rate after LPS injection (FIG. 9).

Platelet aggregation. Venous blood from human volunteer donors was collected in 10 ml Monovette containing 1 ml citrate solution (0.106M trisodium citrate; Sarstedt, Nümbrecht, Germany) and centrifuged (400 g, 10 min, 20° C.). The platelet-rich plasma (PRP) was removed and mixed with one-fourth volume of ACD buffer (44.8 mM sodium citrate, 20.9 mM citric acid, 74.1 mM glucose, pH5.0). After centrifugation (10 min, 2000 g, 20° C.), the platelet pellet was resuspended in washing buffer (113 mM NaCl, 4 mM $Na_2HPO_4$, 24 mM $NaH_2PO_4$, 4 mM KCl, 0.2 mM EGTA (Ethylene glycol-bis-(2-aminoethyl ether) N,N,N'-tetraacetic acid), 0.1% (wt/vol) glucose, pH 6.0) and recentrifuged (10 min, 2000 g, 20° C.). The washed platelets were resuspended in incubation buffer (134 mM NaCl, 12 mM $NaHCO_3$, 2.9 mM KCl, 0.34 mM $NaH_2PO_4$, 5 mM HEPES (N-(2-hydroxyethyl) piperazine-N'-(2-ethanesulfonic acid)), 5 mM glucose, pH7.4), cells were counted in a Sysmex hematology analyzer (Sysmex, CDA-500, Japan) and adjusted to a final concentration of $2 \times 10^8$ platelets/ml.

The aggregation of the platelets in platelet-rich plasma (PRP) was measured as a change in light absorbance by a Payton dual-channel aggregometer (NBS, Hema tracer, Japan). PRP (240 μL) was stirred (700 rpm) at 37° C. for 1 min, and 5 μL epinephrine (final concentration 5 μM), serotonin (final concentration 5 μM) was added, after which the rate of primary aggregation (1/min) and maximum aggregation (%) at 5 min were recorded. To study the effects of compounds on epinephrine or serotonin-induced aggregation, PRP was incubated with 5 μL of compounds at various concentrations for 1 min before epinephrine or serotonin was added. $IC_{50}$ values given were calculated from the secondary aggregation data.

DETAILED DESCRIPTION OF EXPERIMENTS

Intra-cisternal injections. Intra-cisternal injections of eugenosedin-A (0.3, 0.03 μmol), yohimbine (0.03 μmol), and clonidine (38 pmol), were performed in rats as described by Dyan et al (1987). Briefly, rats weighing 250–300 g were anaesthetized with pentobarbital sodium (50 mg kg$^{-1}$, i.p.) and mounted in a David-Kopf stereotaxic instrument (Yeh J L. et al., *Brain. Res. Bull.*, 30:641–648, 1993). The calvarium was exposed and a 1 mm diameter trephine hole was drilled 1.8 mm lateral to the coronary and 1.5 mm posterior to the sagittal sutures. A cannula (0.7 mm O.D.) connected to a Hamilton syringe (RN-705, 5051) by PE-50 was advanced 4.7 mm into the brain using the electrode carrier.

Micro-injection in NTS. Rats were anesthetized and placed in a David-Kopf stereotaxic instrument. The cerebellum was exposed after removing the skin and occipital bone. The NTS coordinates were (reference to lamdar) P 5–6 mm, L/R 0.5–1 mm, depth 6–7.5 mm (Wu et al., 1994). NTS injection sites were confirmed by decreasing BP and HR following micro-injection of 1% L-glutamate. eugenosedin-A (0.3, 0.03 μmol), trazodone (0.3, 0.03 μmol) and yohimbine (0.03 μmol) were then injected. Pretreatment with clonidine was performed 15 min before administration of test agents. At the end of experiments, the animals were sacrificed. The brain was removed and sectioned for histological confirmation of the drug application site.

Isolation of rat thoracic aorta. Rat thoracic aorta was removed, cleaned of adhering fat and connective tissue and cut into 3–4 mm wide transverse rings. These rings were then mounted at 1 g resting tension on stainless steel hooks in a 10 ml organ bath, bathed at 37° C. in physiological solution (mM: NaCl 118, KCl 4.8, $CaCl_2$ 2.5, $MgSO_4$ 1.2, $KH_2PO_4$ 1.2, $NaHCO_3$ 24, glucose 11), and aerated with a 95% $O_2$ and 5% $CO_2$ mixture. Isometric tension of aortic rings was monitored by a force displacement transducer (UGO BASILE, Model 7004, Italy). Tissue was equilibrated for 1 hr in physiological solution (Wu B N. et al., *Br. J. Pharmacol.*, 134:265–274, 2001). Clonidine, noradrenaline and serotonin ($10^{-8} \sim 10^{-4}$M) were added to the bath to induce contractions after pretreatment with eugenosedin-A for 15 min.

Isolation of rat left atria. Rats of either sex weighing 350–500 g were sacrificed after mild anesthesia with ether, and their hearts were quickly excised. Left atria were dissected from the hearts and mounted in a 10 ml organ bath with one end fixed and the other end connected to a force displacement transducer (Grass, Model FT03). The experiments were carried out at 37° C. in a Krebs solution of the following composition (mM): NaCl 113, KCl 4.8, $CaCl_2$ 2.2, $KH_2PO_4$ 1.2, $MgCl_2$ 1.2, $NaHCO_3$ 25, Dextrose 11.0; bubbled with a 95% $O_2$+5% $CO_2$ mixture. Atria were pre-stretched to a baseline tension of 0.5 g and equilibrated for 60 min in an aerated Krebs solution before starting experimental protocols. Atria were driven at 2-s intervals via two platinum electrodes on each side. An incubation time of 30 min was allowed for the test compound. Data were calculated as a percentage of the maximum contraction (Wu et al., 2001).

Receptor binding studies. Wistar rat cortex (for $α_1$, $α_2$-adrenoceptor, serotonergic receptor binding), heart (for $β_1$-adrenoceptor binding), and lung (for $β_2$-adrenoceptor binding) were homogenized with a Kinematica polytron in 20 volumes of ice-cold TE buffer (10 mM Tris HCl, 1 mM EDTA(ethylenediaminetetraacetic acid), 0.1 mM ascorbic acid, pH 7.4) (Wu et al., 1994). The homogenate was pressure filtered through muslin. Filtrate was centrifuged at 1000 g for 10 min. Supernatant was centrifuged at 10,000 g for 12 min at 4° C. The second supernatant was centrifuged at 30,000 g for 15 min at 4° C. The final pellet was re-suspended in assay buffer (75 mM Tris HCl, 25 mM $MgCl_2$, pH 7.4). Protein content was determined by Bradford's method. Radioligand agents and membranes (200–300 μg) were incubated for 60 min at 25° C. with or without the addition of nonspecific binding agents, in a 75 mM Tris HCl buffer with 25 mM $MgCl_2$, to make a final volume of 500 μl. In competitive-binding experiments, the competing agent was added directly to the incubation mixture. Incubation was terminated by addition of 1 ml of ice-cold assay buffer followed by immediate filtration through Whatman GF/C glass fiber filters supported on a 12-port filter manifold (Millipore). The filters were immediately washed 3 times with 5 ml of ice-cold assay buffer and dried in an oven at 60° C. for 2 hours before adding 5 ml of Triton-toluene-based scintillation fluid. Membrane-bound radioligand trapped in the filters was counted in a Beckman LS6500 scintillation system (Fullerton, Calif., U.S.A) with an efficiency of 45%. In each experiment, nonspecifically bound radioligand agents were determined by incubating membrane protein. Specific binding for each sample was obtained by deducting this value from the total binding of radioligand agents.

5-HT re-uptake studies in cerebral cortex. Inhibition of 5-HT reuptake was measured by slight modification of the method of Hatanaka K. et al. (*Neuropharmacology.*, 35:1621–1626, 1996) and Diga M. et al. (*Life. Sci.*, 62:2203–2208, 1998). Wistar rats weighting 150–200 grams were decapitated, the cerebral cortex or striatum was dissected and crude synaptosomes were prepared. The crude synaptosomes were suspended in about 16 mg wet tissue per 1 ml of Krebs buffer for 5-HT uptake. Uptake was initiated by the addition of 50 µl of [3H] 5-ITF to give a final concentration (30 nM), continued for 2 min at 37° C., an terminated by cooling the mixture in an ice bath. Saline was added to the incubation mixture, which was then filtered through a Whatman GF/B glass filter under reduced pressure. To determine nonspecific uptake, incubation was performed at 0° C.

Antioxidant and peroxyl radical scavenging activities. Rat brain homogenate was made in 0.9% saline containing 10 mg tissue/ml. The rates of membrane lipid peroxidation were measured by the formation of thiobarbituric acid (TBA)-reactive substance (TBARS). Rat brain homogenates (1 ml) were incubated at 37° C. for 5 min with 10 µl of test compound or vehicle. Lipid peroxidation was initiated by the addition of 0.1 ml of 0.25 mM $FeCl_2$ and 1 mM ascorbic acid (Huang Y C. et al., *Drug. Dev. Res.*, 47:77–89, 1999). After 30 min of incubation, the reaction was stopped by adding 0.1 ml of 0.2% BHT. TBA reagent was then added and the mixture was heated for 30 min in a boiling water bath. TBARS was extracted by n-butanol and measured at 532 nm. The amount of TBARS was quantified using the linear regression obtained from malondialdehyde (MDA) standards.

The scavenging ability of the test compounds on aqueous peroxyl radicals was determined by the method described by Tasuchiya M. et al. (*Methods Enzymol.*, 213:460–472, 1992). The stoichiometric factors of the test compounds with hydrophilic peroxyl radicals were calculated by the equation as mentioned Ascorbic acid was used as a positive control.

Plasma cytokine immunoreactivity and blood glucose. Blood was collected from venous cannula, injected into ice-cold heparinized Eppendorf tubes and centrifuged at 1500 rpm for 10 min at 4° C. Plasma supernatant was stored at −70° C. until analyzed. Solid phase enzyme immunoassay that specifically detects murine IL-1β, IL-6, IFN-γ and TNF-α was used with a detection limit of >10 pg/ml (Endogen, U.S.A). Pretreatment with eugenosedin-A and other agents was performed 15 minutes before intravenous injection of LPS. Blood was collected from venous cannula. Blood glucose was measured with a glucose test strip (Glucotide, Bayer, U.S.A) at 1, 3 and 5 hours.

Statistical evaluation of data. Results are expressed as mean ±SD. Statistical differences were determined by independent and paired Student's t-test in unpaired and paired samples. Whenever a control group was compared with more than one treated group, the one-way ANOVA or two-way repeated measures ANOVA was used. When the ANOVA manifested a statistical difference, Dunnett's or Student-Newman-Keuls test was applied. P<0.05 was considered to be significant. Analysis of data and plotting of figures were done with the aid of software (SigmaStat and SigmaPlot, Version 5.0, San Rafael, Calif., U.S.A.; Graph-Pad PRISM™, Version 2.0, San Diego, Calif., U.S.A.) run on an IBM-compatible computer and a Power Macintosh.

RESULTS

Depressor and pressor activities. Acute intravenous injection of eugenosedin-A (0.1, 0.5, 1.0 mg $kg^{-1}$) caused mild arterial hypotension in pentobarbital-anesthetized Wistar rats. The depressor effect of eugenosedin-A was less than that of trazodone and ketanserin. There were no significant effects on the BP or HR (FIGS. 2A and 2B).

Intra-cisternal injections of eugenosedin-A (0.3, 0.03 µmol), trazodone (0.3, 0.03 µmol) and yohimbine (0.03 µmol) increased mean arterial BP and HR (FIG. 3A). Eugenosedin-A at 0.3 µmol caused mild pressor responses up to 15 mmHg and increased the HR up to 60 bpm. Yohimbine at a lower dose of 0.03 µmol also induced pressor responses up to 13 mmHg and HR up to 78 bpm. In contrast, microinjection of clonidine (38 pmol) produced long-lasting hypotension (about 10 mmHg) and decreased HR (about 18 bpm) in pentobarbital-anesthetized rats. None of the solvents had a significant effect on BP or HR. Administration of eugenosedin-A, trazodone and yohimbine 15 min before clonidine injection antagonized the hypotensive effect of clonidine (FIG. 3B). Eugenosedin-A at 0.3 µmol reduced the bradycardic effect of clonidine. Neither eugenosedin-A nor yohimbine at 0.03 µmol concentrations antagonized the bradycardic effects of clonidine (FIG. 3B).

Figure 4:
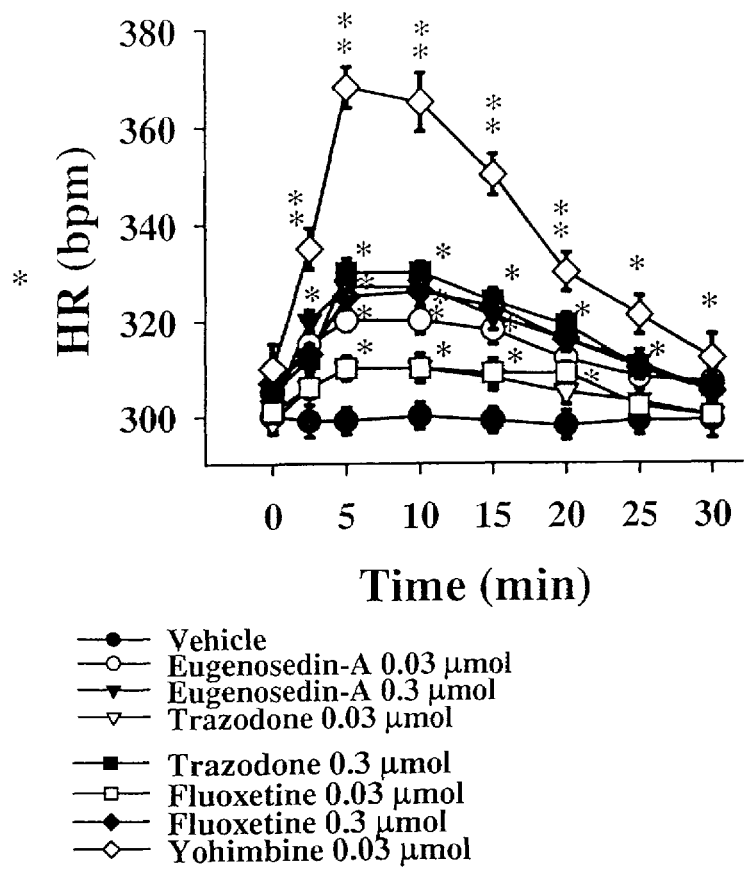
FIG. 4B illustrates HR response of NTS injections of eugenosedin-A, fluoxetine, trazodone and yohimbine in rats for 30 min after injection.

Micro-injection of eugenosedin-A, trazodone and fluoxetine (0.03, 0.3 µmol) in rat NTS produced mild, but significant, pressor responses and increased the HR within 30 minutes after injection. Yohimbine, an $α_2$-adrenoceptor blocker, produced a strong pressor response up to 13 mmHg and HR up to 78 bpm at the lower 0.03 µmol dose (FIG. 4).

Adrenergic receptor antagonist activities. Eugenosedin-A ($10^{-8}$, $10^{-7}$, $10^{-6}$ M) competitively inhibited cumulative noradrenaline- and clonidine-induced contractile activities. As shown in FIGS. 5A and 5B, eugenosedin-A produced a dose-dependent parallel shift to the right of the noradrenaline and clonidine concentration-response curves in isolated rat thoracic aorta (FIG. 5).

Regarding $β_1$-adrenoceptor blocking activity in electrically stimulated left atria, eugenosedin-A ($10^{-8}$, $10^{-7}$, $10^{-6}$ M) concentration-dependently inhibited cumulative isoprenaline-induced positive inotropic effects and produced a dose-dependent parallel shift to the right of isoprenaline-induced concentration-response curves in isolated rat left atria (FIG. 5 D).

$5-HT_{2A}$ receptor antagonist activity. Eugenosedin-A ($10^{-8}$, $10^{-7}$, $10^{-6}$ M) concentration-dependently inhibited cumulatively added 5-HT-induced contractile activities in isolated rat thoracic aorta. Concentration-response curves of 5-HT were dose-dependently parallel-shifted to the right by eugenosedin-A (FIG. 5C).

Receptor binding activity. In this invention, eugenosedin-A, propranolol, prazosin, ketanserin, methysergide and 5-HT all produced competitive binding activities on $α_1$-adrenoceptors, $α_2$-adrenoceptors and serotonergic receptors in rat cortex, respectively, against the following ligands: [3H]prazosin ($α_1$), [3H]yohimbine ($α_2$), [3H]GR125743 ($5-HT_{1B/1D}$), [3H]ketanserin ($5-HT_{2A}$). [3H]CGP-12177 was used in the measurements of competitive binding activities on $β_1$ receptors in rat ventricle and on $β_2$ receptors in rat lung. Eugenosedin-A (Ki=33.29) had a higher binding affinity than propranolol for $5-HT_{2A}$ receptors. Methysergide and 5-HT had lower binding affinities for $α_1$ receptors. Prazosin had strong $\alpha_1$- and $\alpha_2$-adrenoceptor affinities. In contrast, eugenosedin-A's $\alpha_1$-adrenoceptor (Ki=141.94) affinities were lower than prazosin. Ketanserin, methysergide and eugenosedin-A (Ki=1386.14) also had binding affinities for $\alpha_2$-adrenoceptors. Propranolol had high $\beta_1\beta_2$-adrenoceptor affinities. In striking contrast, eugenosedin-A (Ki>10000) had lower binding affinity for $\beta_2$-adrenoceptors.

Inhibitory activities of 5-HT re-uptake. The $IC_{50}$ values of 5-HT uptake inhibition by eugenosedin-A and trazodone in rat cortex were $3.426\times10^{-5}$ M and $1.164\times10^{-6}$ M, respectively. Although eugenosedin-A was not as potent as trazodone, it strongly inhibited 5-HT cortical uptake.

Antioxidant and peroxyl radical scavenging activities. In order to eliminate the possibility that eugenosedin-A and other test compounds interfered with the assay, the test agents were added directly to MDA standard before the TBA reagent was added. Eugenosedin-A dose-dependently inhibited $Fe^{2+}$-ascorbic acid-induced lipid peroxidation in rat brain homogenate with an $IC_{50}$ of $2.681\pm0.05$ µM (n=5).

Figure 6:
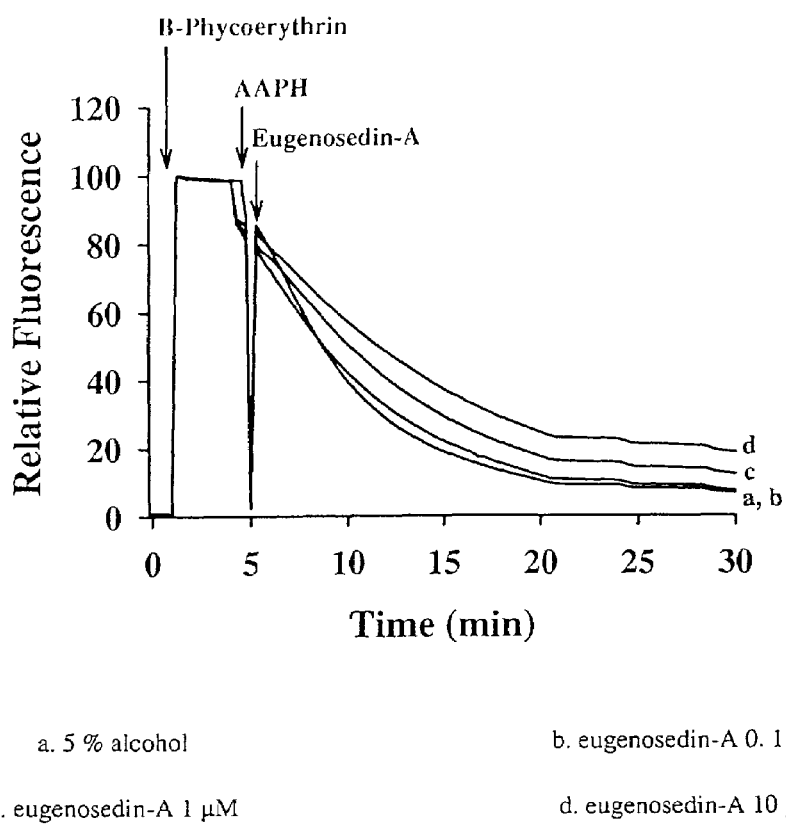
FIG. 6 illustrates protectant agonist effect of eugenosedin-A from hydrophilic peroxyl radical-induced degradation of B-phycoerythrin and AAPH (2,2'-Azobis (2-amidinopropane) dihydrochloride).

Exposure of B-phycoerythrin to AAPH-derived aqueous peroxyl radicals induced a transient decay of fluorescent intensity. Eugenosedin-A produced a concentration-dependent decrement of fluorescence and prolongation of the lag time (FIG. 6). Yohimbine and trazodone did not scavenge peroxyl radicals (data not shown).

Normalization of LPS-induced hypotension. A single injection of LPS (10 mg $kg^{-1}$, i.v.) produced biphasic hypotension: an immediate and transient decrease in BP that was followed by partial recovery within 30 minutes and then followed by prolonged hypotension. The first immediate hypotensive phase was not affected by Pretreatment with eugenosedin-A, yohimbine and trazodone (0.5 mg $kg^{-1}$, i.v.) 30 minutes before LPS injection; however, at higher doses (1 mg $kg^{-1}$. i.v.), they attenuated it. All three significantly reduced the second prolonged hypotensive phase at doses of 0.5 and 1 mg $kg^{-1}$(i.v.), respectively. Aminoguanidine and ascorbic acid (15 mg $kg^{-1}$, i.v.) also inhibited LPS-induced hypotension (FIG. 8). Although BP decreases induced by intravenous eugenosedin-A, trazodone and yohimbine had not completely recovered to earlier levels after 30 minutes, the same dosage of all three drugs prevented further development of hypotension after LPS injection and normalized BP within 5 hours (FIG. 7).

Protective effects on LPS-induced vascular hyporeactivity. Isolated aortas from LPS-treated rats were hyporeactive to phenylephrine ($10^{-8}$~$10^{-4}$M). Intravenous injection of eugenosedin-A (1 mg $kg^{-1}$) before or after application of LPS increased aortic contractility more than the vehicle group. One hour after administration of LPS, vascular contractility was similar to that of controls. In comparison with yohimbine, trazodone, aminoguanidine and ascorbic acid, eugenosedin-A was more effective in protecting from LPS-induced hyporeactivity of the aorta.

Inhibition of LPS-induced cytokine immunoreactivities and hyperglycemia. 1, 3 and 5 hours after LPS 10 mg $kg^{-1}$, i.v.) administration, immunoreactivities of IL-1$\beta$, IL-6, IFN-$\gamma$ and TNF-$\alpha$ were increased. After pretreatment with LPS, none of the administered agents significantly reduced LPS-induced increases in various cytokines. Yohimbine and ascorbic acid insignificantly enhanced LPS-induced production of IFN-$\gamma$ at 1 hour after LPS administration.

However, Pretreatment with eugenosedin-A (1 mg $kg^{-1}$, i.v.) significantly inhibited LPS-induced increases in all these cytokines at 3 hours. Pretreatment with yohimbine, trazodone, aminoguanidine and ascorbic acid also significantly inhibited increases in IL-1$\beta$ and TNF-$\alpha$ at 3 hours. At 5 hours, only eugenosedin, yohimbine and trazodone significantly reduced LPS-induced increases in TNF-$\alpha$ (FIG. 8).

When LPS was not administered, blood glucose levels in rats treated with vehicle as control were not changed. When LPS was administered, hyperglycemia occurred at 1 and 3 hours, followed by progressive hypoglycemia at 5 hours. Eugenosedin-A, aminoguanidine and ascorbic acid all inhibited the initial hyperglycemic response to LPS at 1 and 3 hours; however, they did not reverse the hypoglycemic response at 5 hours (FIG. 9).

Survival rates. As shown in FIG. 10, survival rate at 16 hrs after intravenous injection of LPS (60 mg $kg^{-1}$, i.p.) was zero. However, in comparison with rats without eugenosedin-A pretreatment, those that were pre-treated with eugenosedin-A (0.5, 1, 5 mg $kg^{-1}$, i.p.) had significantly increased LPS-induced survival rates at 12 hrs and the time of LPS-induced death was extended to 36 hrs (FIG. 10).

This inventor evaluated 5-HT re-uptake inhibition and the $5\text{-HT}_{2A}$ and adrenoceptor antagonist activities of eugenosedin-A in the central nervous and cardiovascular systems. Receptor binding studies have indicated that eugenosedin-A has a higher affinity for 5-HT re-uptake sites and $5\text{-HT}_{2A}$ receptors and has a sharply lower affinity for $\alpha$-adrenoceptors than prazosin. Particularly, it increased blood pressure by microinjection into cisternal and NTS. These facts encouraged us to examine whether eugenosedin-A offers protection against LPS-induced hypotension and mortality.

Intra-cisternal injection and NTS microinjection of eugenosedin-A, trazodone and yohimbine increased BP and HR. In fact, injection of the selective $\alpha_2$ antagonist yohimbine into the NTS produced hypertension and tachycardia, possibly because yohimbine antagonizes the postsynaptic effects of endogenously released catecholamines (Kubo et al., 1987). This inventor's results also confirmed that central administration of yohimbine increased BP and HR (Corrêa and Peres-Polon, 1995; Díaz-Cabiale et al., 2000). In our experiment, low dose (0.03 µmol) eugenosedin-A and yohimbine reduced the centrally effective $\alpha_2$-adrenoceptor agonist clonidine-induced hypotension, but did not inhibit clonidine-induced bradycardia. At a high dose (0.3 µmol), eugenosedin-A reduced both clonidine-induced hypotension and bradycardia. Since clonidine-like drugs owe part of their bradycardic effect to activation of peripheral cardiac pre-synaptic $\alpha_2$-autoreceptors (Urban et al., 1995), the invention theorize that eugenosedin-A and yohimbine at lower doses had no significant effect on peripheral cardiac pre-synaptic $\alpha$-autoreceptors. Minimum autonomic activity has been attributed to fluoxetine, and microinjection of this substance into the NTS increased BP and HR (Lane and Baldwin., 1997).

Three subtypes of $\alpha_2$-adrenoceptors, designated as $\alpha_{2A}$, $\alpha_{2B}$ and $\alpha_{2C}$, were proposed by Murphy et al. (1988). The $\alpha_{2A}$-adrenergic subtype is located in the CNS and is concentrated in the cardiovascular control center of the brainstem. $\alpha_{2B}$-adrenergic receptors are located in arterial vascular smooth muscle cells and cause peripheral vasoconstriction (MacMillan et al., 1996; Duka et al., 2000). It is obvious that $\alpha_{2B}$-adrenoceptor agonist activity of clonidine in thoracic aorta produces contractile activity (Fujimoto and Itoh., 1995). The inventor proposed that eugenosedin-A-mediated inhibition of clonidine-induced contraction is caused by antagonist activity on $\alpha_2$-adrenergic receptors.

Figure 3D:
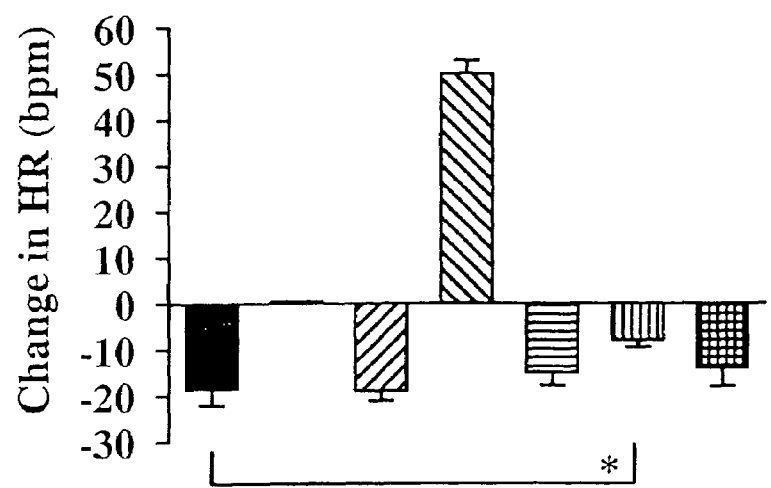
FIG. 3D illustrates the antagonistic effects of intra-cisternal injections of eugenosedin-A and yohimbine after pretreatment with clonidine on HR (heart rate).

Antagonist activity of eugenosedin-A on $\alpha_2$-adrenoceptors might prevent agonist-induced vasocontraction, thereby lowering BP. However, pressor $\alpha_2$-adrenoceptor antagonist activity of eugenosedin-A in the CNS, administered at a dose 0.3 µmol (close to intravenous dose 0.1 mg kg$^{-1}$), contrasted to the depressor response in the peripheral nervous system mediated by vascular $\alpha_1$- and $\alpha_2$-adrenoceptors. The yohimbine-like central pressor effect of eugenosedin-A (FIG. 3), might be partially masked by a peripheral $\alpha_1$-adrenoceptor blocking-associated depressor response.

Several pharmacologic studies have indicated that $^5$-HT$_{2A}$ receptors mediate the contractile response of blood vessels (Le Roux and Syce, 1989). It has been suggested that both 5-HT$_{2A}$ and 5-HT$_{1B}$ receptors are involved in vascular contraction (Smith et al., 1999). In the isolated rat aorta experiments, eugenosedin-A also produced a dose-dependent parallel shift to the right in 5-HT-induced concentration-response curves (FIG. 5). Based on these results, the invention suggests that eugenosedin-A is a 5-HT$_2$ receptor antagonist.

Reduction of vascular smooth muscle contractility by ketanserin in the presence of 5-HT is due to inhibition of serotonergic receptors, stimulation of a-adrenoceptors or the interaction between serotonergic and a-adrenergic activation (Curro et al., 1978). On the other hand, the antidepressant trazodone has mild $\alpha_1$-adrenergic receptor antagonist activity, in addition to its action on $\alpha_2$-adrenergic and 5-HT receptors (Krege et al., 2000). Eugenosedin-A, which has a similar CPB structure to that of trazodone, produces same serotonergic and adrenergic effects. Antagonist activity of eugenosedin-A on 5-HT$_{2A}$ receptors in vascular tissue might partially prevent 5-HT-induced vasocontraction. In isolated rat aorta, the estimated pA$_2$ value (8.68±0.12) for eugenosedin-A indicated that its antagonist activity on 5-HT$_{2A}$ receptors was more potent than on $\alpha_1$- and $\alpha_2$-adrenoceptors, respectively. In comparison with ketanserin, eugenosedin-A displayed less affinity for 5-HT$_{2A}$ receptors and $\alpha_1$-adrenoceptors. It is reasonable that the depressor effect of eugenosedin-A was less than that of ketanserin (FIG. 2B).

Aryloxypropanolamines are generally recognized as β-adrenoceptor blockers. In pentobarbital-anesthetized rats, intravenous administration of eugenosedin-A produced a dose-dependent decrease in mean BP and HR and also inhibited phenylephrine- and isoprenaline-induced changes in BP and HR. Eugenosedin-A, an isoeugenol-based aryloxypropanolamine, antagonized isoprenaline-induced positive inotropic effects on isolated rat left atrial strips and showed some binding affinity for β$_1$-adrenoceptors (FIG. 5).

Stimulation by increased plasma catecholamines during early sepsis may cause sympathetic activation of the CVS (Lavicky and Dunn., 1995; Molina-Holgado and Guaza., 1996). This β-adrenergic receptor stimulation may also exercise a beneficial agonist effect on macrophages to increase cAMP and to decrease inflammatory cytokines (Szelényi et al., 2000). The non-selective β-adrenoceptor blocker propranolol prevents the effects of $\alpha_2$-adrenoceptor blockade on TNF-α plasma levels induced by LPS and associated cytokine formation in mice (Haskó et al., 1995; Elenkov et al., 1995). Eugenosedin-A, which has $\alpha_2$- and selective β$_1$-adrenergic antagonist, but not β$_2$-adrenergic antagonist activities, inhibited LPS-induced increases in TNF-αplasma levels (FIG. 5). β-adrenoceptors may be down-regulated and unable to respond fully to catecholamine-derived β-adrenoceptor agonist and drug-derived β-adrenergic antagonist activities during sepsis. In contrast to previous studies of pindolol (Ko et al., 2002), eugenosedin-A displayed pindolol-like serotonergic and β-adrenoceptor blocking properties that might contribute to its protective effects against LPS-induced hypotension, vascular hyporeactivity and cytokine formation (FIGS. 7, 8 and 9).

A reciprocally permissive interaction occurs between TNF-α and α-adrenoceptor activation. Changes in presynaptic adrenergic sensitivity, as well as in neuronal sensitivity to TNF-α have been implicated in the action of antidepressant drugs (Nickola et al., 2001). Previous studies have demonstrated a neuro-immune link that enables stress-associated noradrenaline to regulate macrophage-derived TNF via α-adrenergic receptor interactions. Both noradrenaline and $\alpha_2$-adrenergic agonists have been shown to augment LPS-induced TNF production. This augmentation was prevented by the $\alpha_2$-adrenergic antagonist yohimbine (Borysenko, 1984; Glaser et al., 1986; Spengler et al., 1990).

Intravenous LPS in this invention produced a biphasic reduction in BP in anesthetized rats (Lin et al., 1999). Both aortic hyporeactivity and the second prolonged hypotensive reaction induced by LPS were inhibited by pretreatments with eugenosedin-A, yohimbine and trazodone. They all significantly reduced LPS-induced production of IL-1β and TNF-α at 3 hours (FIG. 8). These facts indicate that $\alpha_2$-adrenoceptor blockade plays an important role in normalizing LPS-induced hypotension (Szelényi et al., 2000).

Reactive oxygen species, superoxides in particular, have been implicated in the potentiation of iNOS induction in cells (Wu et al., 2002). iNOS inhibitors and antioxidants reduce LPS-induced vascular hyporesponsiveness (Girard et al., 1995; Ülker et al., 2001). Likewise, the antioxidant activity of eugenosedin-A, absent in trazodone and yohimbine, may provide more protection against LPS-induced aortic hyporeactivity and hypotension. NO in the CNS is increased by both the $\alpha_2$-adrenoceptor agonist clonidine and LPS administration. The action of clonidine is dependent on activation of eNOS. The action of LPS is dependent on activation of iNOS (Tseng et al., 1996; Dobrucki et al., 2001). The inventor thus suggested that both clonidine- and LPS-induced hypotension are partly attributed to NO release, which are inhibited by the effects of aminoguanidine on iNOS and by the antagonist activities of eugenosedin-A on $\alpha_2$-adrenoceptors.

Antioxidants can ameliorate depression of vascular reactivity caused by LPS (Loegering et al., 1995). Among them, ascorbic acid affected macrophage activity in mice during endotoxic shock (Victor et al., 2000). In this regard, the toxic effects of oxygen radicals produced by immune cells can be controlled to certain degree by endogenous antioxidants (Victor et al., 2000). LPS-induced elevations of IL-1β, IL-6, IFN-γ and TNF-α levels were inhibited by eugenosedin-A (1 mg kg$^{-1}$, i.v.). Trazodone and yohimbine in the same doses reduced only IL-1β and TNF-α. This difference might be due to eugenosedin-A's antioxidant activity, which more potently reduces LPS-induced cytokine production. In this regard, the relationship between the antioxidant effect of eugenosedin-A and its anti-hypotensive/hyporeactivity effects might relate to the inhibition on cytokine-induced iNOS production (Wu et al., 2002).

The generation of free radicals in biological systems contributes to oxidative stress, including inflammation (Girard et al., 1995). Eugenosedin-A possesses free radical scavenging and anti-peroxidation properties that yohimbine and trazodone lack. This may also account for the fact that eugenosedin-A more potently reduces LPS-induced hypotension and vascular hyporeactivity than yohimbine and trazodone.

Endotoxicosis causes many metabolic alterations. Hyperglycemia in the early phase of sepsis is caused by a decrease in peripheral tissue glucose uptake relative to the rate of glucose production. In contrast, hypoglycemia in severe septic conditions occurs because the rate of glucose use exceeds the rate of production (Maitra et al., 2000). In the present study, LPS-induced early hyperglycemia at 1 and 3 hours was inhibited by eugenosedin-A, aminoguanidine and ascorbic acid. However, they did not affect the hypoglycemia at 5 hours. Atenolol, a selective $\beta_1$-adrenergic blocker, does not alter the glucose metabolic response to infection. Under septic conditions, non-selective β-adrenoceptor blocker propranolol prevents an increase in glucose production (Lang, 1992). Since eugenosedin-A is a selective $\beta_1$-adrenoceptor blocker, but not a $\beta_2$-adrenoceptor blocker, suggest that it, like aminoguanidine, inhibits LPS-induced hyperglycemia by decreasing glycogenolysis and gluconeogenesis (Sugita et al., 2002).

Many pathobiochemical alterations occur in endotoxic shock: dramatic increase in eicosanoid and platelet activation factor production, cytokine release (in particular IL and TNF-α, activation of the L-arginine-nitric oxide (NO) pathway, formation of oxygen-centered free radicals and activation of the plasmatic coagulation cascade, fibrinolysis and complement pathway (Szabò and Thiemermann, 1994). In this invention, eugenosedin-A reduced LPS-induced hypotension-associated cytokine formation. Although cytokine levels were not completely inhibited by eugenosedin-A during the later stage of LPS-induced hypotension, eugenosedin-A was beneficial in treating the early stage of LPS-induced hypotension. This suggests that other events are involved in the pathogenesis of LPS-induced mortality. In this invention, even though eugenosedin-A did not prevent LPS-induced death, it did prolong survival time. The prolongation of survival and prevention of early hypotension might provide some clinical benefits in improving overall survival of patients in septic shock.

In conclusion, eugenosedin-A has adrenergic and serotonergic antagonist activities, including possible pindolol-like characteristics. It can reduce and potentially normalize LPS-induced hypotension, as well as generate a CNS-mediated increase in BP. Eugenosedin-A has an antioxidant effect that may contribute to its ability to reduce LPS-induced hypotension and other endotoxic inflammatory responses. Further evaluation of eugenosedin-A's antidepressant-related behavior activities is still needed. It is notable that $\alpha_2$-Adrenoceptor blocking properties of eugenosedin-A and other phenylpiperazine type antidepressants may be beneficial in the treatment of septic shock. Eugenosedin-A's effects, including its $\beta_1$ adrenoceptor blocking activity, on bacteria-induced hypotension requires further investigation.

EXAMPLE 1

1-(2 chlorophenyl-1-piperazinyl)-2-propanol-3-oxy-(2-methoxy-propenyl)-benzene or 1-((2-methoxy-4-propylenyl)-phenoxy)-3-((2chlorophenyl-piperazinyl)-2-propanol (1).

Epichlorohydrin 100 ml was mixed with isoeugenol 20 ml and NaOH 10 g dissolved in ethanol 10 ml, boiled to reflux for 4 hours. Obtained mixture was removed the included ethanol and passed through silica gel column chromatography, eluated with n-hexane and ethyl acetate (9:1), dryed with reduced pressure and obtained 4-epoxy isoeugenol (63 g).

2-chlorophenyl piperazine (5 g) was dissolved in methanol (20 ml), mixed with 4-epoxy isoeugenol (20 g), and boiled to reflux at 80° C. for 4 hours. Obtained mixture was then removed the included methanol by reduced pressure using vacuum pump. The residue was passed through silica gel column chromatography, eluated with n-hexane and ethyl acetate (9:1), dried by reduced pressure, and crystallized with methanol to obtain 19.8 g white crystal of compound 1.

$^1$H NMR (CDCl$_3$)δ0.07 (CH$_3$), 1.84–1.89 (d, 3H, Ar—CH=CH—C$\underline{H}_3$), 2.62–2.69 (m, 2H, Ar—O—CH$_2$CH (OH)—C$\underline{H}_2$—N), 2.72–2.91 (t, 4H, 2×Ar—N—CH$_2$C$\underline{H}_2$—N—), 3.07–3.12 (t, 4H, 2×Ar—N—CH$_2$C$\underline{H}_2$—N—), 3.74–3.87 (d, 3H, Ar—O—C$\underline{H}_3$), 4.02–4.05 (m, 2H, Ar—O—C$\underline{H}_2$CH—(OH)—CH$_2$—N), 4.12–4.21 (m, 2H,ArOCH$_2$C$\underline{H}$—(OH)—CH$_2$—N), 6.02–6.29 (m, 1H, ArCH=C$\underline{H}$—CH3), 6.30–6.39 (d, 1H, ArC$\underline{H}$=CHCH3), 6.81–7.07 (m, 6H, Ar), 7.18–7.38 (m, 6H, Ar—Cl); IR (KBr) 3450, 2935, 2821 cm$^{-1}$; MS m/z 417 (M+H)$^+$.

The pharmacological compositions that are created with the compound of this invention will include various excipients; carriers or diluents and pharmaceutically approved processed salts in accordance with the necessity to form composition with therapeutic efficacy. Such pharmaceutical preparation could be in solid form for oral and/or rectum administration; liquid form or non-intestinal injection form; or ointment form for direct application on an affected part. Such solid forms are manufactured according to common pharmaceutical preparation methods, which would typically include a disintegrant like starch; sodium carboxymethylcellulose, adhesive like ethanol; glycerine, or magnesium stearic acid; lactose to make into pharmaceutical preparation like tablets or filled into capsules or suppository. Solution or saline that include this invention compound as ingredient could use buffers of phosphoric nature to adjust the pH to suitable level, before adding adjutant; emulsifier to produce injection dose or other liquid preparation. This invention compound or pharmaceutical manufacturing could be mixed with synthetic acid salts with various fundamental preparations to form ointments according to known pharmaceutical manufacturing methods. Pharmaceutical compositions manufactured with this invention compound being the major ingredient could be used on mammals to produce the efficacy of this main ingredient. General dosage could be adjusted according to the degree of symptoms, and normally a person will require 50 to 300 mg each time, three times per day.

What is claimed is:

1. A compound having the following formula:

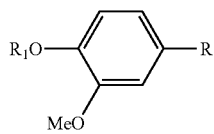

Formula I

Wherein R is a 1-propenyl group;
Wherein R$_1$ is:

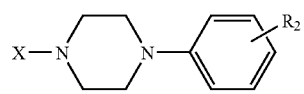

where X is:

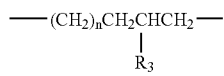

wherein $R_2$ is one selected from the group consisting of a halogen F, Cl, Br and I, n is 0, and $R_2$ is positioned at one or more of the following positions o-, m-, or p- on the benzene ring, and $R_3$ is OH group.

2. A method for preparing isoeugenol derivative compounds having the following formula:

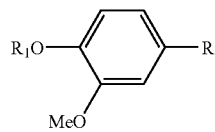

wherein R is a 1-propenyl group;
wherein $R_1$ is:

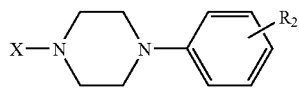

where X is:

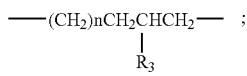

wherein $R_2$ is one selected from the group consisting of a halogen F, Cl, Br and I, n is 0, and $R_2$ is positioned at one or more of the following positions o-, m-, or p- on the benzene ring, and wherein $R_3$ is OH group, said method comprising the steps of:

mixing Epichlorohydrin with isoeugenol and NaOH dissolved in ethanol to create a mixture;

boiling said mixture to reflux for 2–6 hours to remove said ethanol;

passing said mixture through silica gel column chromatography, eluting said mixture with n-hexane and ethyl acetate, drying said mixture with reduced pressure to create a dried mixture;

mixing said dried mixture with piperazine dissolved in methanol to reflux at 100° for 2–6 hours to obtain a second mixture;

removing the methanol from the second mixture by reduced pressure using a vacuum pump to leave a residue;

passing said residue through silica gel column chromatography;

eluting said residue with n-hexane and ethyl acetate;

drying said residue by reduced pressure; and crystallizing said residue with methanol to obtain a white crystal of compound.

3. A pharmaceutical composition having one activity selected from a group consisting of $\alpha_2$-adrenergic/5-HT$_{2A}$ antagonist activity, 5-HT re-uptake inhibition activity and anti-oxidant activity, comprising a quantity of the compound described in claim 1, and a preselected quantity of diluents and excipients.

* * * * *